(12) United States Patent
Donnelly et al.

(10) Patent No.: US 8,216,811 B2
(45) Date of Patent: Jul. 10, 2012

(54) METHODS FOR CONVERTING GLUCOSE TO ASCORBIC ACID

(75) Inventors: Mark Donnelly, Warrensville, IL (US); William H. Eschenfeldt, St. Charles, IL (US); Jonathan Trent, La Silva Beach, CA (US)

(73) Assignee: Danisco US Inc., Palo Alto, CA (US)

( * ) Notice: Subject to any disclaimer, the term of this patent is extended or adjusted under 35 U.S.C. 154(b) by 0 days.

(21) Appl. No.: 13/041,176

(22) Filed: Mar. 4, 2011

(65) Prior Publication Data
US 2011/0229943 A1 Sep. 22, 2011

Related U.S. Application Data

(60) Continuation of application No. 12/487,497, filed on Jun. 18, 2009, now Pat. No. 7,922,483, which is a continuation of application No. 12/050,455, filed on Mar. 18, 2008, now Pat. No. 7,563,609, which is a division of application No. 11/015,039, filed on Dec. 17, 2004, now Pat. No. 7,374,917, which is a continuation of application No. 10/418,401, filed on Apr. 17, 2003, now Pat. No. 6,864,075, which is a division of application No. 09/684,385, filed on Oct. 4, 2000, now Pat. No. 6,576,452.

(51) Int. Cl.
| | |
|---|---|
| *C12P 7/00* | (2006.01) |
| *C12P 21/04* | (2006.01) |
| *C12N 9/02* | (2006.01) |
| *C12N 1/20* | (2006.01) |
| *C12N 15/00* | (2006.01) |
| *C12Q 1/26* | (2006.01) |
| *C07H 21/04* | (2006.01) |

(52) U.S. Cl. ............ 435/132; 435/189; 435/252.3; 435/320.1; 435/69.1; 435/71.1; 435/25; 536/23.2

(58) Field of Classification Search .................. None
See application file for complete search history.

(56) References Cited

U.S. PATENT DOCUMENTS

| | | | | |
|---|---|---|---|---|
| 3,922,194 | A | 11/1975 | Sonoyama et al. | 195/30 |
| 4,179,337 | A | 12/1979 | Davis et al. | 435/181 |
| 4,301,144 | A | 11/1981 | Iwashita et al. | 424/78 |
| 4,496,689 | A | 1/1985 | Mitra | 525/54.1 |
| 4,640,835 | A | 2/1987 | Shimizu et al. | 424/94 |
| 4,670,417 | A | 6/1987 | Iwasaki et al. | 514/6 |
| 4,791,192 | A | 12/1988 | Nakagawa et al. | 530/399 |
| 5,795,761 | A | 8/1998 | Powers et al. | 435/190 |
| 5,912,161 | A | 6/1999 | Hurle et al. | 435/252.2 |

FOREIGN PATENT DOCUMENTS

| | | |
|---|---|---|
| WO | 87/00863 | 2/1987 |
| WO | 87/05330 | 9/1987 |

OTHER PUBLICATIONS

Branden et al. Introduction to Protein Structure, Garland Publishing Inc., New York, p. 247, 1991.*

Altschul et al., "Basic Local Alignment Search Tool," J. Mol. Biol., V. 215, 1990, pp. 403-410.
Altschul el et al., "Gapped BLAST and PSI-BLAST: a new generation of protein database programs," Nucl. Acids Res., vol. 25, pp. 3389-3402, 1997.
Altschul et al., "Basic Local Alignment Statistics," Methods in Enzymology, V. 266, pp. 460-480 (1996).
Anderson et al., "Production of 2-Keto-L-Gulonate, an Intermediate in L-Ascorbate Synthesis, by a Genetically Modified *Erwinia herbicola,*" Science, vol. 230, Oct. 11, 1985, pp. 144-149.
Aplin et al., "Preparation, Properties, and Applications of Carbohydrate Conjugates of Proteins and Lipids," Crit. Rev. in Biochem. 1981, pp. 259-306.
Ausubel, Frederick et al., "Short Protocols in Molecular Biology," Current Protocols in Molecular Biology, 2nd ed., Greene Publishing Associates & John Wiley & Sons. New York, N.Y. 1992.
Ausubel et al., Ed. Current Protocols in Molecular Biology, John Wiley & Sons, Inc. Ch. 9, 1988.
Batzer et al., "Enhanced evolutionary PCR using oligonucleotides with inosine at the 3'-terminus", Nucl. Acids Res., vol. 19, p. 5081, 1991.
Blattner et al., "The Complete Genome Sequence of *Escherichia coli* K-12," Science, vol. 277, pp. 1453-1462, 1997.
Davey et al., "Ascorbate Biosynthesis in *Arabidopsis* Cell Suspension Culture," Plant Physiol. vol. 121, pp. 535-543, 1999.
Devereux et al., "A Comprehensive set of sequence analysis programs for the VAX," Nucl. Acids Res., vol. 12, p. 387-395, 1984.
Eschenfeldt et al., "DNA from Uncultured Organisms as a Source of 2,5-Kiketo-D-Gluconic Acid Reductases," Applied and Environmental Microbiology, V. 67 (9), Sep. 2001, p. 4206-4214.
Edge et al., "Deglycosylation of Glycoproteins by Trifluoromethanesulfonic Acid," J. Med. Chem., vol. 30, pp. 1229-1239, 1987.
Evan et al., "Isolation of Monoclonal Antibodies Specific for Human c-myc Proto-Oncogene Product," Mol. and Cell. Biology, vol. 5, pp. 3610-3616, 1985.
Feng et al., "Progressive Sequence Alignment as a Prerequisite to Correct Phylogenetic Tress" J. Mol Evol. vol. 25, pp. 351-360, 1987.
Field et al., "Purification of a RAS-Responsive Adenylyl Cyclase Complex from *Saccharomyces cerevisiae* by Use of an Epitope Addition Method," Mol. and Cell. Biology, vol. 8, pp. 21592165, 1988.
Furste et al., "Molecular cloning of the plasmid PR4 primase region in a multi-host-range tacP expression vector," Gene, vol. 48, pp. 119-131, 1986.
Goding, J., "Production of Monoclonal Antibodies," Monoclonal Antibodies: Principle and Practice, 1986, pp. 59-103.
Grindley, J. F, "Conversion of Glucose to 2-Keto-L-Gulonate, an Intermediate in L-Ascorbate Synthesis, by a Recombinant Strain of *Erwinia citreus,*" Applied and Environmental Microbiology, vol. 54, No. 7, Jul. 1988, p. 1770-1775.

(Continued)

Primary Examiner — Yong Pak
(74) Attorney, Agent, or Firm — Danisco US Inc.

(57) ABSTRACT

Described herein are novel nucleic acids, proteins and methods that can be used to provide new catalysts with desirable traits for industrial processes. In particular, novel reductases isolated from the environment using PCR methods are described.

1 Claim, 8 Drawing Sheets

OTHER PUBLICATIONS

Hakimuddin et al., "A Chemical Method for the Deglycosylation of Proteins," *Archives of Biochem. and Biophysics*, vol. 159, 1987, p. 52-57.

Higgins et al., "Fast and sensitive multiple sequence alignments on microcomputer," *CABIOS*, vol. 5, 1989, p. 151-153.

Hopp et al., "A short polypeptide marker sequence useful for recombinant protein identification and purification," *Bio/Tech.*, vol. 6, 1988, p. 1204-1210.

Jez et al., "Comparative anatomy of the aldo-keto reductase superfamily," *Bioch. J.*, vol. 326, 1997, pp. 625-636.

Khurana et al., "Crystal structure of 2,5-diketo-D-gluconic acid reductase A complexed with NADPH at 2.1-A resolution," *Proc. Natl. Acad. Sci. USA*, vol. 95, pp. 6768-6773, Jun. 1998 Biophysics.

Karlin et al., "Applications and statistics for multiple high-scoring segments in molecular sequences," Proc. Natl. Acad. Sci. USA, vol. 90, pp. 5873-5877, Jun. 1993.

Kohler et al., "Continuous cultures of fused cells secreting antibody of predefined specificity," Nature, vol. 256, pp. 495-497, 1975.

Laemmli U. K. "Cleavage of Structural Proteins during the Assembly of the Head of Bacteriophage T4," Nature, vol. 227, pp. 680-685, 1970.

Lutz-Freyermuth, "Quantitative determination that one of two potential RNA-binding domains of the A protein component of the U1 small nuclear ribonucleoprotein complex binds with high affinity to stem-loop II of U1 RNA," Proc. Natl. Acad. Sci. USA, vol. 87, pp. 6393-6397, 1990.

Maniatis et al., Molecular Cloning: A Laboratory Manual, 2d Edition, 1989.

Martin et al., "GAP Domains Responsible for Ras p21-Dependent Inhibition of Muscarinic Atrial K+ Channel Currents," *Science*, vol. 255, (1992), pp. 192-194.

Miller, J. H., "Purification and Characterization of 2,5-Diketo-D-gluconate Reductase from Corynebacterium Sp," *J. Biol. Chem.*, vol. 262, (1987), pp. 9016-9020.

Needleman et al., "A General Method Applicable to the Search for Similarities in the Amino Acid Sequence of Two Proteins," *J. Mol. Biol.*, vol. 48, pp. 443-453, 1970.

Nishikimi et al., "Biochemistry and Molecular Biology of Ascorbic Acid Biosynthesis," *Subcell. Biochemistry*, pp. 17-39, 1996.

Ohtsuka et al., "An Alternative Approach to Deoxyoligonucleotides as Hybridization Probes by Insertion of Deoxyinosine at Ambiguous Codon Positions" (1985) *J. Biol. Chem.* vol. 260, No. 5, pp. 2605-2608.

Paborsky et al., "Mammalian cell transient expression of tissue factor for the production of antigen," Protein. Engin. vol. 3, pp. 547-553, 1990.

Pearson et al., "Improved tools for biological sequence comparison," Proc. Natl. Acad. Sci. USA, vol. 85, pp. 2444-2448, Apr. 1988.

Ratnam et al., "The Argine 276 Anchor for NADP(H) Dictates Fluorescence Kinetic Transients in 3α-Hydroxysteroid Dehydrogenase, a Representative Aldo-Keto Reductase," Biochemistry, vol. 38, pp. 7856-7864 (1999).

Redenbach et al., "A set of ordered cosmids and a detailed genetic and physical map for the 8 Mb *Streptomyces coelicolor* A3(2) chromosome," Mol. Microb., vol. 21, pp. 77-96 (1996).

Rossolini et al., "Use of deoxyinosine-containing primers vs degenerate primers for polymerase chain reaction based on ambiguous sequence information" (1994) *Mol Cell. Probes* 8, 91-98.

Sarkar et al., "Restriction-site PCR: A Direct Method of Unknown Sequence Retrieval Adjacent to a Known Locus by Using Universal Primers," *PCR Methods and Applic.* vol. 2, 318-322 (1993).

Sambrook et al., Molecular Cloning: A Laboratory Manual, New York: Cold Spring Harbor Press, 1989.

Seery et al., "Molecular Evolution of the Aldo-keto Reductase Gene Superfamily," *J. Mol. Evol.*, vol. 46, pp. 139-146 (1998).

Selenska et al., "DNA Recovery and Direct detection of Tn5 sequences from soil," *Letters in Applied Microbiol.*, vol. 13, pp. 21-24, (1991).

Skinner et al., "Use of the Glu-Glu-Phe C-terminal Epitope for Rapid Purification of the Catalytic Domain of Normal and Mutant ras GTPase-activating Proteins," *J.Biol. Chem.* vol. 266, pp. 14163-14166 (1991).

Smith et al., "Comparison of Biosequences," Adv. In App. Math. vol. 2, pp. 482-489, 1981.

Sonoyama et al., "Purification and Properties of Two 2,5-Diketo-D-Gliconate Reductases from a Mutant Srrain Derived from Corynebacterium sp," J. Ferment. Technol., vol. 65, pp. 311-317, 1987.

Thotakura et al., "Enzymatic Deglycosylation of Glycoproteins," Methods in Enzymology, V. 138, pp. 350-359 (1987).

Tijssen, "Hybrydization with Nucleic Acid Probes—Overview of Principles of Hybridization and the Strategy of Nucleic Acid Probes", Techniques in Biochem. and Mol. Biol., (1993).

Todaka et al., "Purification and Characterization of NAD-Dependent Morphine 6-Dehydrogenase from Hamster Liver Cytosol, a New Member of the Aldo-Keto Reductase Superfamily", Arch. of Biochem. and Bioph., V. 374, pp. 189-197 (2000).

Wheeler et al., "The Biosynthetic pathway of Vitamin C in Higher plants", Nature. V. 393, pp. 365-369 (1998).

Willey et al., "Nucleotide sequence and over-expression of morphine dehydrogenase, a plasmid-encoded gene from *Pseudomonas putida* M-10", Biochem. J., V. 290, pp. 539-544 (1993).

Yum et al., "The yiaE Gene, Located at 80.1 Minutes on the *Escherichia coli* Chromosome, Encodes a 2-Ketoaldonate Reductase", J. of Bacteriology, V. 180, pp. 5984-5988 (1998).

Yum et al., "Identification of the yqhE and yafB Genes Encoding Two 2,5-Diketo-D-Gluconate Reductases in *Escherichia coli*", App. and Envir. Microbiol., V. 65, pp. 3341-3346 (1999).

\* cited by examiner

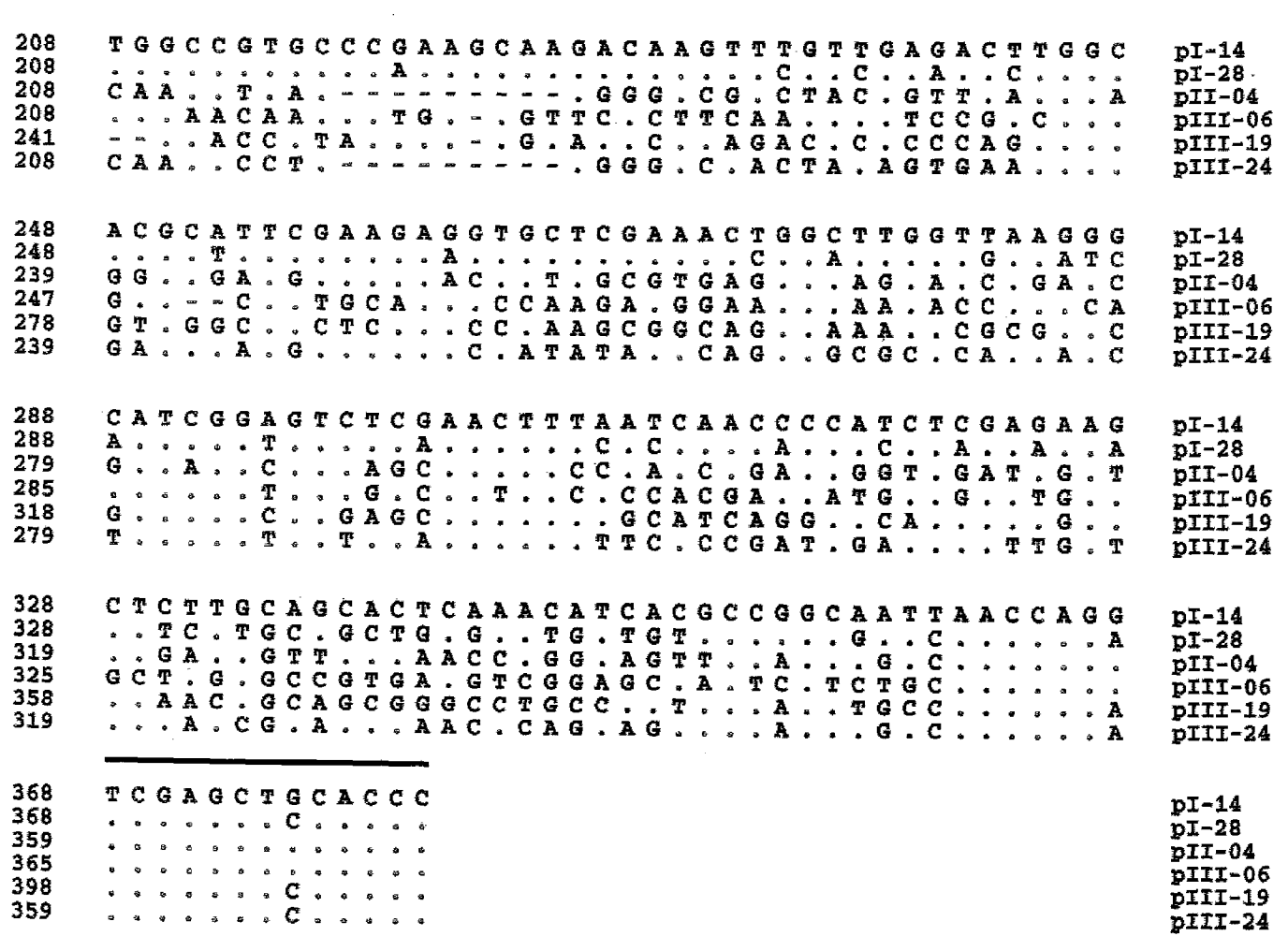

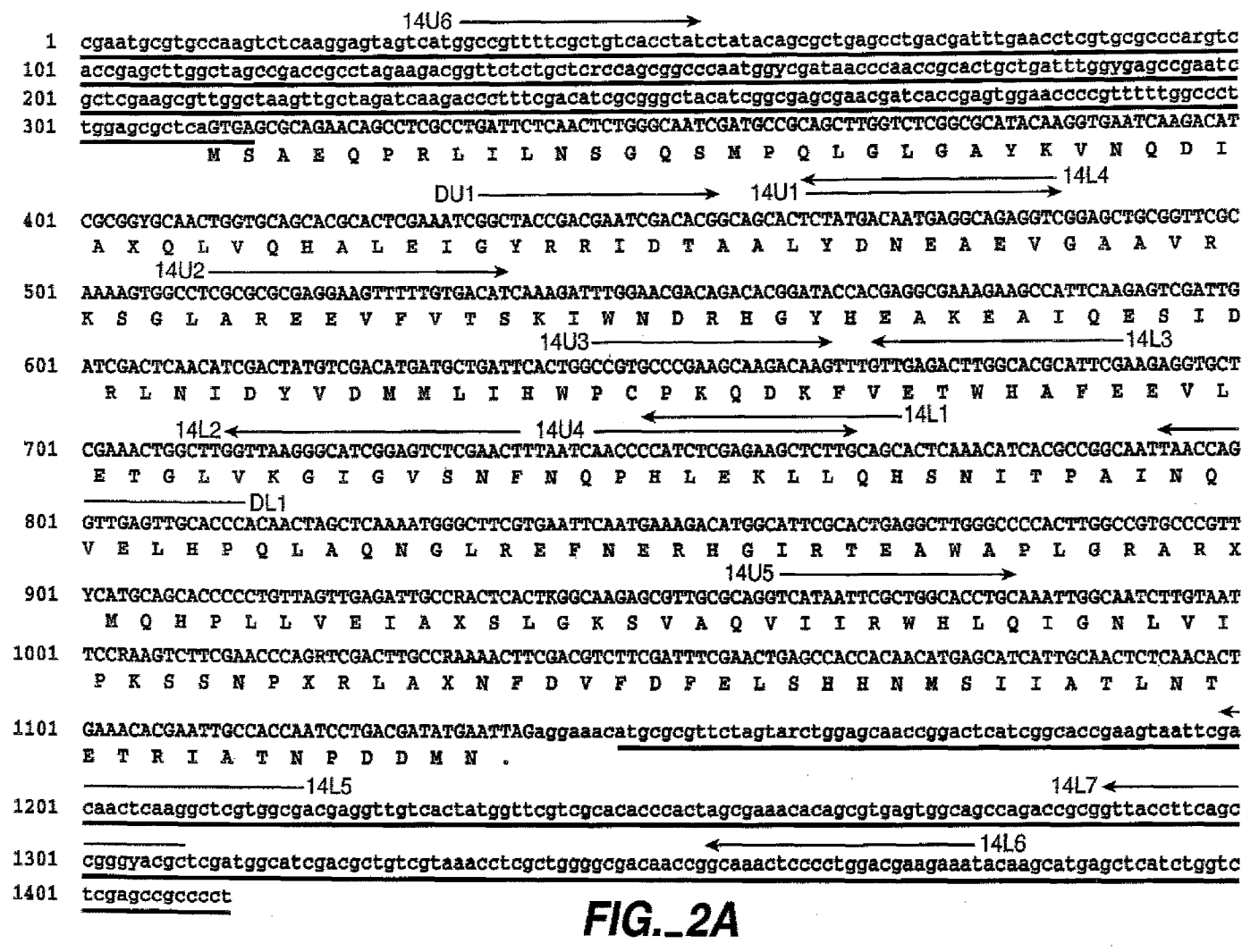

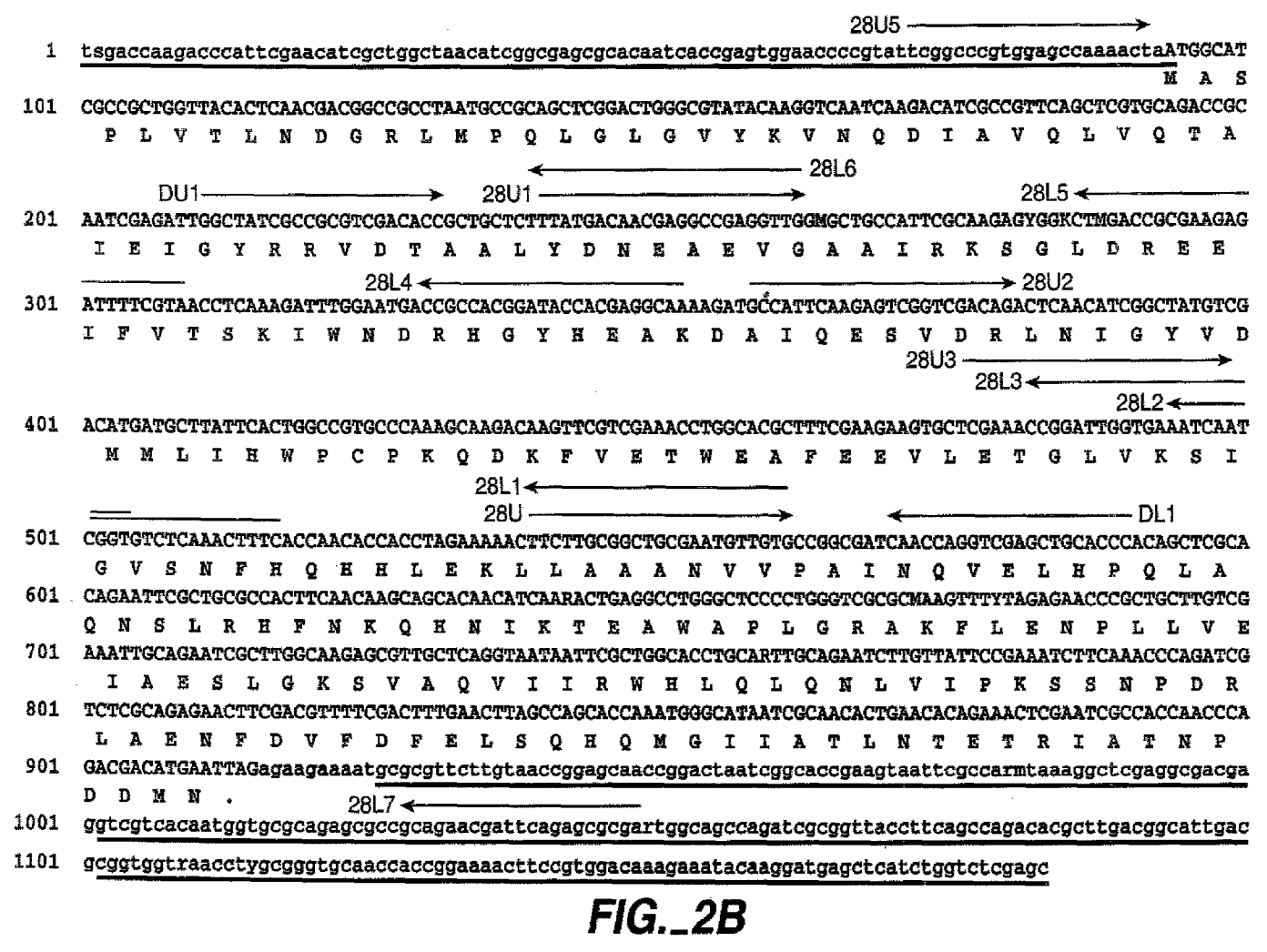

```
  1 MSAEQPRLILNSGQSMPQLGLGAYKVNQDITVQLVQHALE  pI-14
  1 MAS..LVT..D.RL............A..T.I.         pI-28

41 IGYRRIDTAAIYDNEAEVGAAVRKSGLAREEVFVTSKIWN  pI-14
 39 ...V......L.........I...E......H.I....    pI-28

81 DRHGYHEAKEAIQESIDRLNIDYVDMMLIHWPCPKQDKFV  pI-14
 79 ..........V......G..........             pI-28

121 ETWHAFEEVLETGLVKGIGVSNFNQPHLEKLLQHSNITPA  pI-14
119 ..........S.......H..AAATVV.              pI-28

161 INQVELHPQLAQNGLRENERHGIRTEAWAPLGRARFMQH   pI-14
159 ......S..HF.KQ.N..K.K.LEN                 pI-28

201 PLLIEIAESLGKSVAQVIIRWHLQIGNLVIPKSSNPDRLA  pI-14
199 ..V...............LQ.                     pI-28

241 ENFDVFDFELSHHNMSIIATLNTETRIATNPDDMN       pI-14
239 ..........Q.Q..G                          pI-28
```

FIG._3

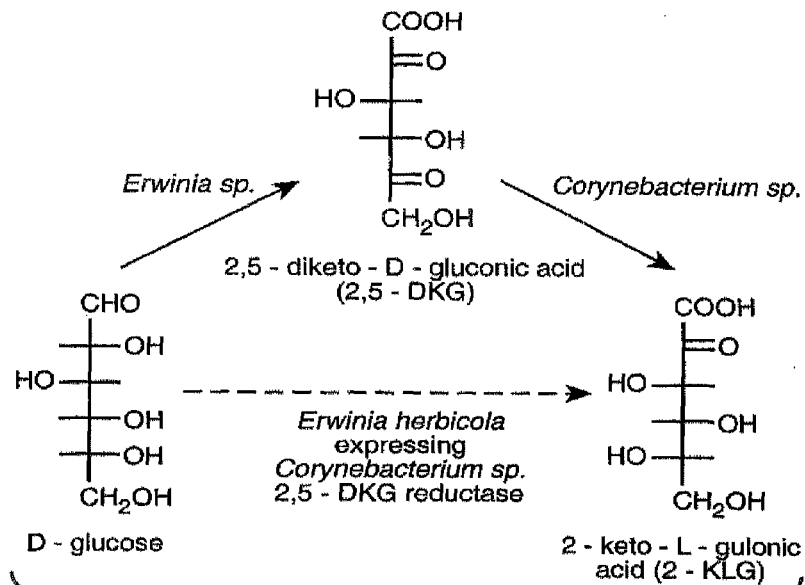
FIG._4
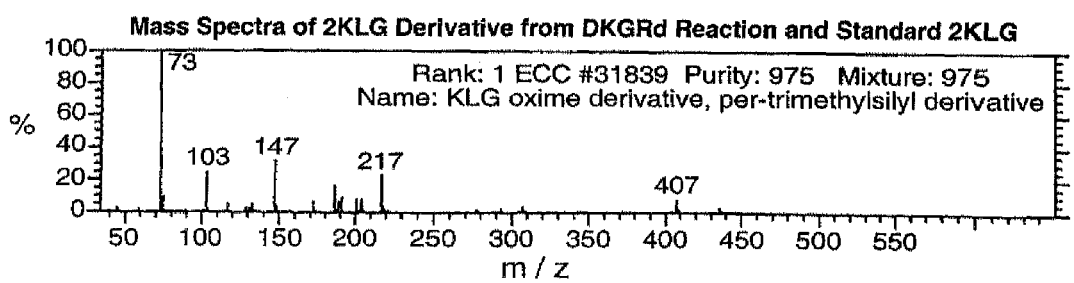
FIG._5A
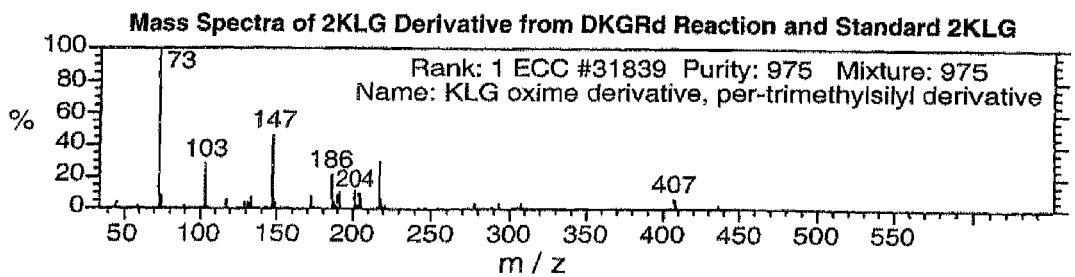
FIG._5B

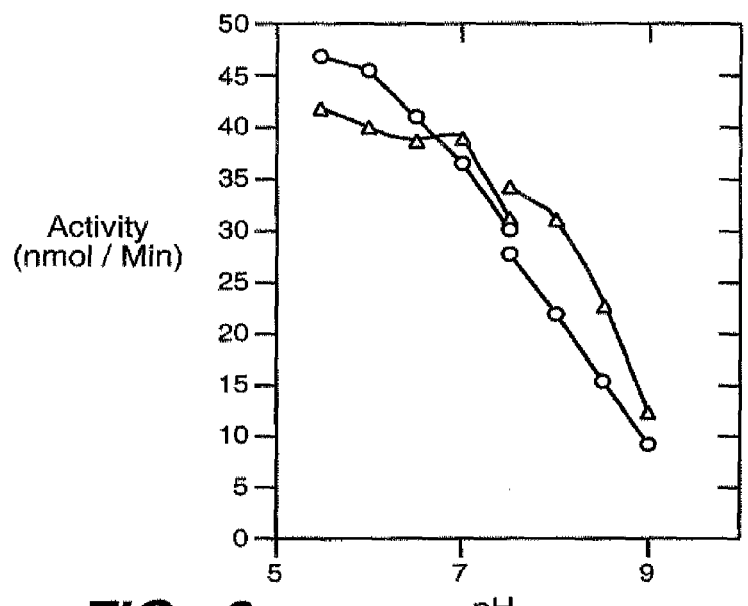
FIG._6
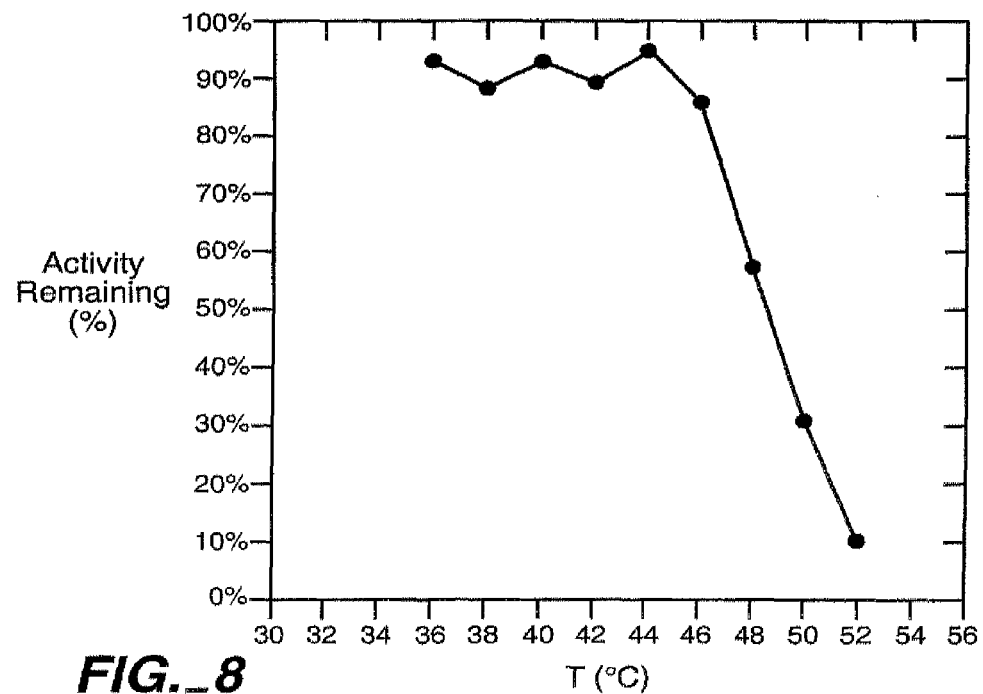
FIG._8

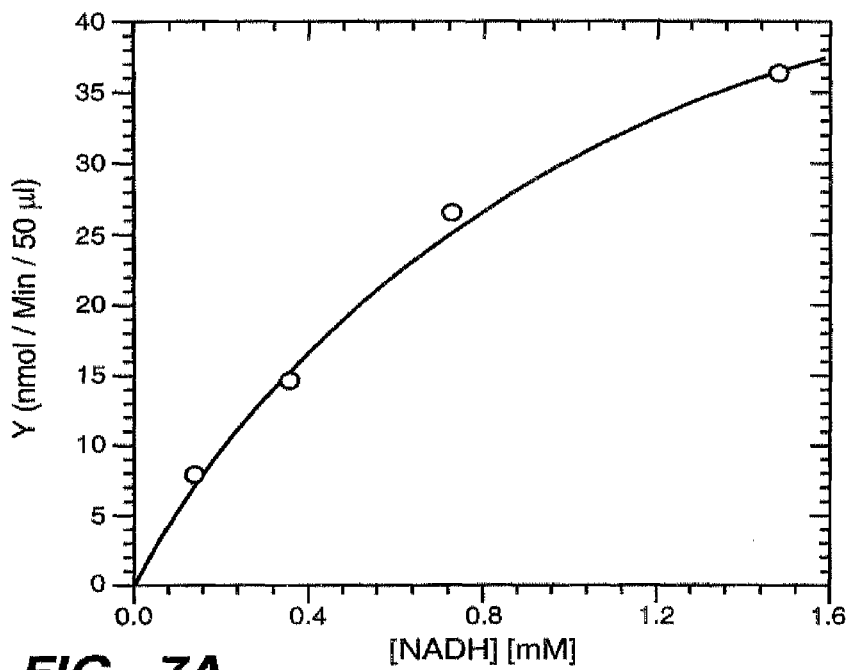
FIG._7A
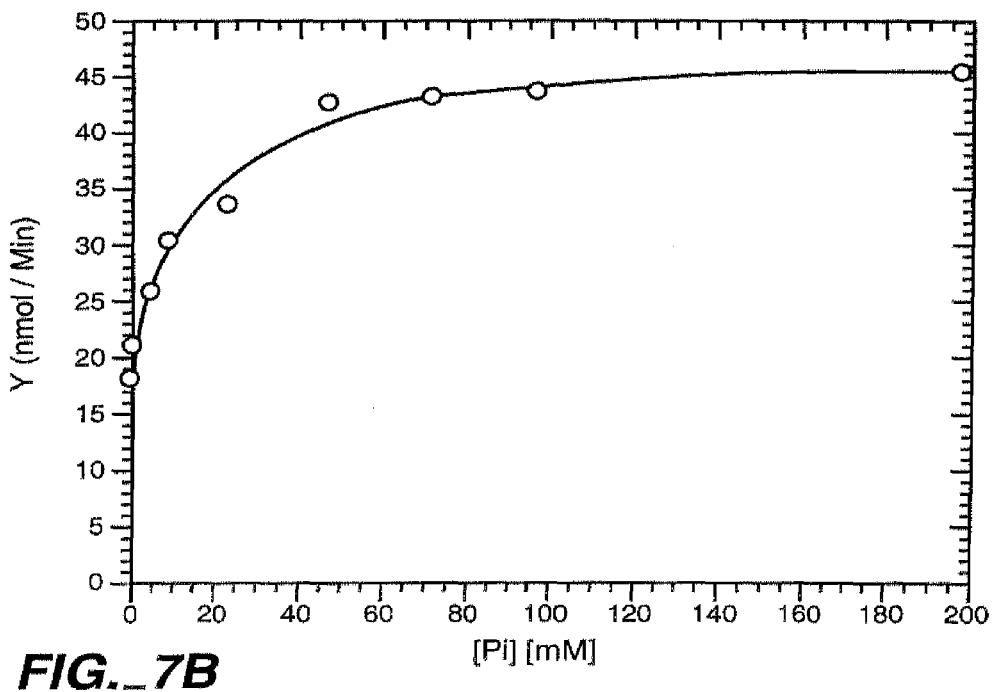
FIG._7B

METHODS FOR CONVERTING GLUCOSE TO ASCORBIC ACID

REFERENCE TO RELATED APPLICATIONS

This application is a continuation of application Ser. No. 12/487,497, filed Jun. 18, 2009, now U.S. Pat. No. 7,922,483, which is a continuation of application Ser. No. 12/050,455, filed Mar. 18, 2008, now U.S. Pat. No. 7,563,609, which is a divisional of application Ser. No. 11/015,039, filed Dec. 17, 2004, now U.S. Pat. No. 7,374,917, which is a continuation of U.S. application Ser. No. 10/418,401, filed Apr. 17, 2003, now U.S. Pat. No. 6,864,075, which is a divisional of application Ser. No. 09/684,385, filed Oct. 4, 2000, now U.S. Pat. No. 6,576,452.

STATEMENT AS TO RIGHTS TO INVENTIONS MADE UNDER FEDERALLY SPONSORED RESEARCH AND DEVELOPMENT

This invention was made with United States Government support under Award No. 70 NANB 5H1138 awarded by the United States Department Of Commerce. The Government has certain rights in this invention.

FIELD OF THE INVENTION

The present invention relates to naturally occurring and recombinant variants of 2,5-diketo-D-gluconic acid reductase. More specifically, the invention relates to the isolation, identification and use of 2,5-diketo-D-gluconic acid reductases.

BACKGROUND OF THE INVENTION

Conversion of glucose to vitamin C (ascorbic acid) is a complicated process because it involves the selective epimerization, oxidation, and lactone formation. The natural biosynthetic pathways are long and incorporate many energy-consuming reactions (Davey, et al., *Plant Physiol.* 121(2):535-43 (1999); Nishikimi, M and K. Yagi, *Subcell Biochem.* 25:17-39 (1996); Wheeler, et al., *Nature* 393(6683):365-9 (1998). The current commercial process for ascorbic acid production (the Reichstein process) couples a single, initial biological step— the microbial reduction of glucose to sorbitol—with subsequent, multi-step chemical conversion of blocked derivatives of sorbitol to ascorbic acid (Crawford, T. C., *American Chemical Society*, Washington, D.C. (1982); Reichstein, T. and A. Grussner, *Helv. Chim. Acta* 16:311 (1934)). An alternative commercial process has been proposed that consists of biological conversion of glucose to 2-keto-L-gulonic acid which is lactonized chemically to ascorbic acid (Anderson, et al., *Science* 230:144-149 (1985); Grindley, et al., *Appl. Environ. Microbiol.* 54:1770-1775 (1988); Sonoyama, et al., U.S. Pat. No. 3,922,194 (1975)). The biological metabolism involved is simpler than that of natural biosynthetic routes and requires less metabolic energy (less ATP and NADPH). In this process, glucose is first converted to 2,5-diketo-D-gluconic acid by endogenous oxidases of a suitable bacterial strain using molecular oxygen as the ultimate electron acceptor. 2,5-diketo-D-gluconic acid is then reduced enzymatically to 2-keto-L-gulonic acid by a heterologous 2,5-diketo-D-gluconic acid reductase (DKGR) expressed in the production strain. The NADPH required for the reaction is generated by the metabolism of the host strain. Finally, chemical lactonization of 2-keto-L-gulonic acid generates ascorbic acid.

To date, only two 2,5-diketo-D-gluconic acid reductases have been extensively characterized, both isolated from a species of *Corynebacterium* (Miller, et al., *J. Biol. Chem.* 262(19):9016-20; Powers, D. B. and S. Anderson, U.S. Pat. No. 5,795,761 (1998); Sonoyama, T. and K. Kobayashi, *J. Ferment. Technol.* 65:311-317 (1987)). These enzymes are able to reduce 2,5-diketo-D-gluconic acid, but alternative or altered reductases could improve ascorbic acid production by the process described above or variations of it. Both of the *Corynebacterium* enzymes are relatively inefficient catalysts, exhibiting $K_m$ values for 2,5-diketo-D-gluconic acid greater than 1 mM and catalytic efficiencies ($k_{cat}/K_m$) less than 20 $mM^{-1}sec^{-1}$.

2,5-diketo-D-gluconic acid reductases are members of the aldo-keto reductase superfamily (Jez, et al., *Biochem J.* 326 (Pt3):625-36 (1997); Seery, et al., *J Mol. Evol.* 46(2):139-46 (1998)). Like almost all other aldo-keto reductases, the known 2,5-diketo-D-gluconic acid reductases are exclusively specific for NADPH (Jez, et al., *Biochem J.* 326 (Pt3):625-36 (1997); Seery, *J Mol Evol.* 46(2):139-46 (1998)). Recently, additional aldo-keto reductases that can convert 2,5-diketo-D-gluconic acid to 2-keto-L-gulonic acid have been isolated from *E. coli* based on a search of the genome sequence (Yum, et al., *Bacteriol.* 180(22):5984-8 (1998); Yum, et al., *Appl Environ Microbiol.* 65(8):3341-6 (1999)). However, these enzymes also catalyze the reaction relatively inefficiently. The known 2,5-diketo-D-gluconic acid reductases also lack stability; both *Corynebacterium* enzymes are thermally labile (Powers, D. B. and S. Anderson, U.S. Pat. No. 5,795,761 (1998); Sonoyama, T. and K. Kobayashi, *J. Ferment. Technol.* 65:311-317 (1987)).

It would therefore be desirable to solve the problem of inefficient reductases by providing 2,5-diketo-D-gluconic acid reductases which are more efficient than known reductases. In particular, it would be desirable to provide novel enzymes which display greater catalytic efficiency than previously known 2,5-diketo-D-gluconic acid reductases, and which have NADH-dependant activity. It would further be desirable for the reductase to be more stable thermally than known 2,5-diketo-D-gluconic acid reductases. It would further be desirable to provide variants of said reductases, methods of making, screening and using novel reductases.

SUMMARY OF THE INVENTION

The present invention provides nucleic acids, proteins, microorganisms and methods of making and using the same, which each involve reductases of the superfamily of aldo-keto reductases.

In one embodiment, an isolated nucleic acid molecule comprising a nucleic acid sequence which encodes a peptide having an amino acid sequence which has at least about 60% sequence identity to an amino acid sequence as set forth in FIG. 2A (SEQ ID NO:8) or 2B (SEQ ID NO:10) is provided. In another embodiment, said nucleic acid molecule consists essentially of said nucleic acid sequence. In another embodiment, said amino acid sequence has at least about 70%, 80%, or as much as 90% sequence identity to said amino acid sequence of FIG. 2A (SEQ ID NO:8) or 2B (SEQ ID NO:10). Fragments of said nucleic acids are also provided herein.

In another embodiment, the isolated nucleic acid molecule provided herein comprises a nucleotide sequence as set forth in FIG. 2A (SEQ ID NO:7) or 2B (SEQ ID NO:9), or a fragment thereof.

In another aspect of the invention, an isolated nucleic acid molecule is provided herein which comprises a sequence having at least about 50%, 55%, or 60% sequence identity to a sequence selected from the group of sequences set forth in FIG. 1 (SEQ ID NOs:1-6). In another embodiment, said nucleic acid molecule consists essentially of a sequence having at least about 50%, 55%, or 60% identity to a sequence of FIG. 1 (SEQ ID NOs:1-6). In another embodiment, said sequence has at least about 70%, 80%, or as much as 90% sequence identity to said sequence of FIG. 1 (SEQ ID NOs: 1-6). In another embodiment, a nucleic acid is provided herein which has a sequence selected from the sequences as set forth in FIG. 1 (SEQ ID NOs:1-6). Fragments of said nucleic acids are also provided herein.

In yet a further embodiment, a nucleic acid provided herein encodes a protein having activity of a reductase from the aldo-keto reductase superfamily. In preferred embodiments, said protein comprises 2,5-diketo-D-gluconic acid reductase activity.

Also provided herein is an expression vector comprising any one or more of the nucleotide sequences provided herein. Also provided herein is a microorganism comprising one or more of said vectors. Preferably, said microorganism is of *Pantoea*.

Further provided herein is polypeptide comprising an amino acid sequence having at least about 60% identity to an amino acid sequence as set forth in FIG. 2A (SEQ ID NO:8) or 2B (SEQ ID NO:10). Preferably, said polypeptide comprises 2,5-diketo-D-gluconic acid reductase activity. In another embodiment, said polypeptide has at least 70% sequence identity with said amino acid sequence of FIG. 2A (SEQ ID NO:8) or 2B (SEQ ID NO:10). In a further embodiment a polypeptide is provided herein that has an amino acid sequence as set forth in FIG. 2A (SEQ ID NO:8) or 2B (SEQ ID NO:10). Fragments of the polypeptides provided herein are also provided.

In yet a further aspect of the invention, provided herein are variants of the nucleic acids and polypeptides provided herein. Generally, the variants are mutated internally and/or at the amino and/or carboxyl terminus so as to have an altered activity from the wildtype. In one embodiment, said polypeptide has a Q at a position corresponding to position 232 and/or position 238 of the amino acid sequence shown in FIG. 2A (SEQ ID NO:8).

In preferred embodiments, reductases are provided herein which have one or more improved or altered qualities or characteristics over previously known reductases. In one embodiment, said reductase has improved catalytic efficiency. In another embodiment, said reductase has NADH dependent activity. In another embodiment, said reductase has improved thermal stability. In another embodiment, said reductase has increased solvent tolerance. In another embodiment, said reductase has an altered pH optimum.

Also provided herein is a process for converting glucose to ascorbic acid comprising culturing the host cells provided herein under conditions suitable for the expression of 2,5-diketo-D-gluconic acid reductase.

In yet a further aspect of the invention, a method for identifying a 2,5-diketo-L-gluconic acid reductase is provided which comprises isolating nucleic acid molecules having homology to 2,5-diketo-L-gluconic acid reductases from uncultured microorganisms and screening said molecules for 2,5-diketo-D-gluconic acid reductase activity, wherein said molecules having 2,5-diketo-D-gluconic acid reductase activity are identified as a 2,5-diketo-L-gluconic acid reductase.

Other aspects of the invention will become apparent by the detailed description of the application which follows.

BRIEF DESCRIPTION OF THE DRAWINGS

FIG. 1 shows the alignment of the nucleotide sequences (SEQ ID NO:1-6) of the six environmental DNA PCR products. The entire sequence of clone pI-14 is shown. Identical bases in the remaining sequences are indicated by dots (.). Gaps introduced into the alignment are indicated as dashes (-). The solid bars indicate the locations of the two degenerate PCR primers.

FIG. 2 shows the nucleotide sequences of the full-length clones for pI-14 (FIG. 2A (SEQ ID NO:7)) and pI-28 (FIG. 2B (SEQ ID NO:9)). The coding region for the putative reductase genes are indicated in capitol letters with the deduced amino acid sequence (SEQ ID NO:8 and SEQ ID NO:10, respectively) shown immediately underneath in single letter code. Locations of the degenerate and clone-specific primers are indicated by arrows. The putative partial open reading frames upstream and downstream from the reductase gene are indicated by solid bars.

FIG. 3 shows the alignment of the deduced amino acid sequences of clones pI-14 (SEQ ID NO:8) and pI-28 (SEQ ID NO:10). The entire sequence of pI-14 is shown. Identical bases in clone pI-28 are indicated by dots (.).

FIG. 4 depicts a recombinant process for the conversion of glucose to ascorbic acid.

FIG. 5 depicts mass spectra of 2-keto-L-gulonic acid reaction product and 2-keto-L-gulonic acid standard. FIG. 5A shows the mass spectrum of the 2-keto-L-gulonic acid reaction product. FIG. 5B shows the mass spectrum of the 2-keto-L-gulonic acid standard.

FIG. 6 depicts the dependence of the rate of reaction on pH.

FIG. 7 depicts the NADH-dependent 2,5-diketo-D-gluconic acid activity of environmentally isolated 2,5-diketo-D-gluconic acid reductases. FIG. 7A shows the NADH dependent activity and FIG. 7B illustrates enhancement of NADH-dependent activity by inclusion of inorganic phosphate.

FIG. 8 depicts the thermal stability of 2,5-diketo-D-gluconic acid reductase environmental form d (DKGRd).

DETAILED DESCRIPTION OF THE INVENTION

Provided herein are novel proteins and the nucleic acids. Also provided herein are the use of said proteins and nucleic acids. Further provided herein are methods for the isolation and production of said proteins and nucleic acids. Moreover, in one aspect of the invention, proteins provided herein have been identified as belonging within the family of aldo-keto reductases and in preferred embodiments, are 2,5-diketo-D-gluconic acid reductases.

A protein having 2,5-diketo-D-gluconic acid reductase (DKGR) activity is defined herein as a protein which is capable of catalyzing the conversion of 2,5-diketo-D-gluconic acid to 2-keto-L-gulonic acid. In preferred embodiments, the 2,5-diketo-D-gluconic acid reductases provided herein may accept either NADPH or NADH as cosubstrate. In one embodiment, both are substrates. In another embodiment, DKGR can serve as a carbon or sugar source. In yet another embodiment, DKGR has other activities of reductases, particularly aldo-keto reductases.

It is understood that herein, the DKGR protein and nucleic acid can be referred to herein as "DKGR sequences" wherein the context will indicate whether the sequence is an amino acid sequence, nucleic acid sequence, or either.

Figure 1A:
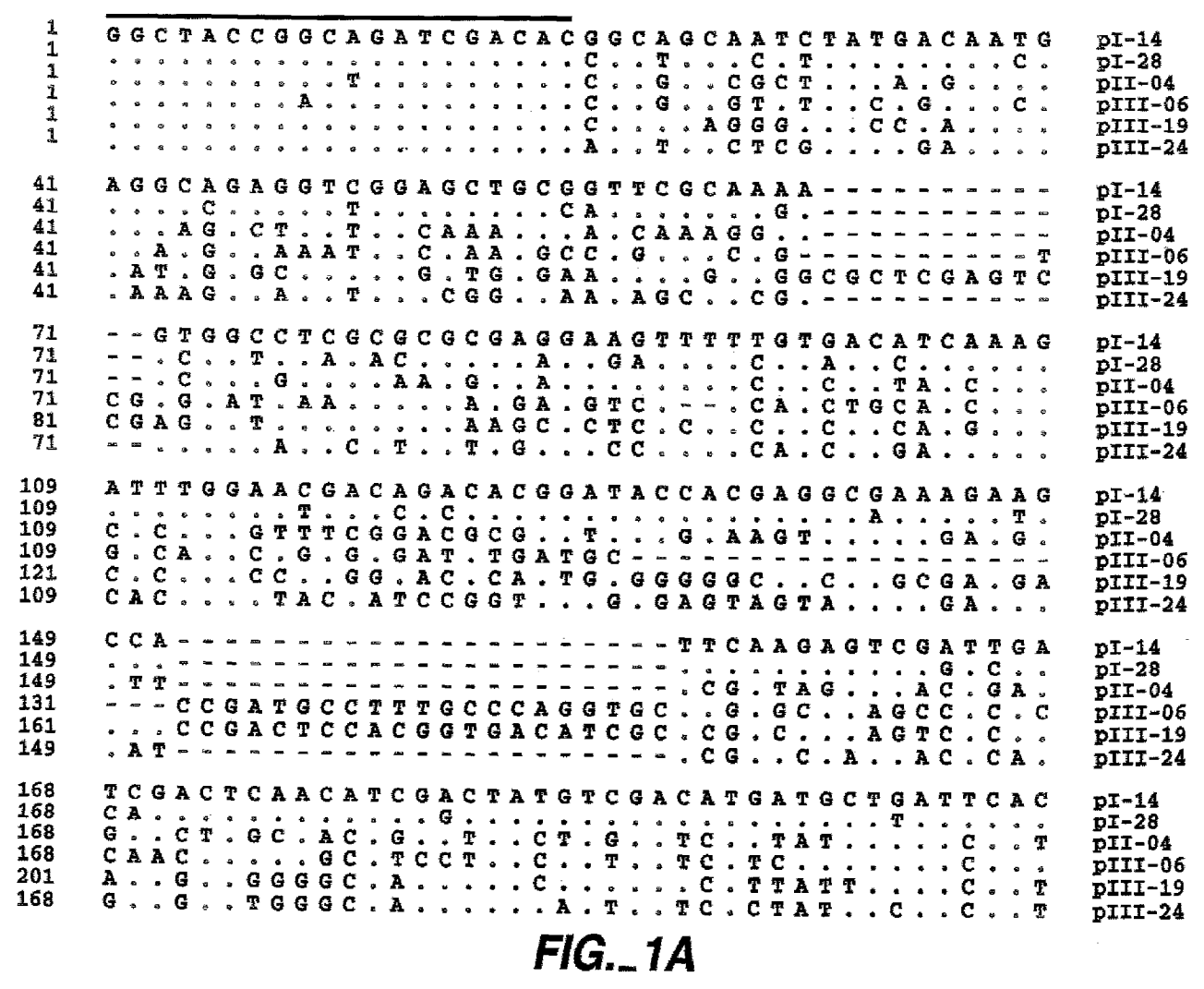

In one aspect of the invention, the DKGR proteins provided herein have altered properties over previously described DKGRs. Properties which may be altered include one or more of the following but are not limited to catalytic efficiency, NADH dependent activity, thermal stability, solvent tolerance, specificity and pH optimum. Altered means that a detectable change has occurred, usually an increase or decrease of at least 10%, more preferably 30%, more preferably 75%, more preferably 100%, and more preferably at least 2 or 3 times more. Preferably, the property of catalytic efficiency, thermal stability or solvent tolerance is improved. Additionally, as further described below, the sequences provided herein can be altered or used to generate DKGR proteins which have an altered property compared to the DKGR proteins of FIG. 2 or encoded by the sequences shown in FIG. 1.

In one embodiment, a DKGR sequence can be initially identified using degenerate PCR primers derived from sequence information of DKGRs previously published or as described herein. Putative full-length genes are first obtained using successive PCR steps in which the specificity of the reaction increases with each step in the nesting process. To verify that the full length gene obtained by this approach represents a naturally occurring gene sequence, the complete gene is amplified directly from the starting sample of environmental DNA using PCR primers targeting the flanking regions of the predicted sequences.

In other embodiments, a DKGR sequence can be identified by substantial nucleic acid and/or amino acid sequence homology to the DKGR sequences outlined herein. Such homology can be based upon the overall nucleic acid or amino acid sequence, and is generally determined as outlined below, using either homology programs or hybridization conditions.

Thus, in one embodiment, a nucleic acid is a "DKGR nucleic acid" if the overall homology of the nucleic acid sequence to the nucleic acid sequences of the Figures (the nucleic acid Figures) is preferably greater than about 50%, more preferably greater than about 55%, 60% or 70%, more preferably greater than about 80%, even more preferably greater than about 85% and most preferably greater than 90%. In some embodiments the homology will be as high as about 93 to 95 or 98%. Homology as used herein is in reference to sequence similarity or identity, with identity being preferred. This homology will be determined using standard techniques known in the art, including, but not limited to, the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, PNAS USA 85:2444 (1988), by computerized implementations of these algorithms (GAP, BESTFIT, FASTA, and TFASTA in the Wisconsin Genetics Software Package, Genetics Computer Group, 575 Science Drive, Madison, Wis.), the Best Fit sequence program described by Devereux, et al., *Nucl. Acid Res.* 12:387-395 (1984), preferably using the default settings, or by inspection.

In a preferred embodiment, the nucleic acids provided herein encode a DKGR protein which has at least 55%, 60% or 65% overall identity and/or 75% overall similarity to a sequence encoded by the sequences of FIG. 1, and preferably to a sequence as shown in FIGS. 2A, 2B or FIG. 3. More preferably, the nucleic acids provided herein encode proteins having at least 85% or 90% identity and/or 90% similarity to said sequences. Fragments of nucleic acids are also provided. Preferred fragments are those which encode preferred protein fragments which are discussed below.

One example of a useful algorithm is PILEUP. PILEUP creates a multiple sequence alignment from a group of related sequences using progressive, pairwise alignments. It can also plot a tree showing the clustering relationships used to create the alignment. PILEUP uses a simplification of the progressive alignment method of Feng & Doolittle, *J. Mol. Evol.* 35:351-360 (1987); the method is similar to that described by Higgins & Sharp *CABIOS* 5:151-153 (1989). Useful PILEUP parameters including a default gap weight of 3.00, a default gap length weight of 0.10, and weighted end gaps.

In a preferred embodiment, multiple sequence analysis is done using the Lasergene program suite from DNASTAR. DNASTAR uses the Clustal algorithm in the Megalign program version 3.12. Default multiple alignment parameters include a gap penalty of 10 and a gap length penalty of 10. Pairwise alignment default parameters include Ktuple of 1, a gap penalty of 3; a window of 5 and diagonals saved of 5.

Another example of a useful algorithm is the BLAST algorithm, described in Altschul, et al., *J. Mol. Biol.* 215, 403-410, (1990) and Karlin, et al., *PNAS USA* 90:5873-5787 (1993). A particularly useful BLAST program is the WU-BLAST-2 program which was obtained from Altschul, et al., *Methods in Enzymology* 266: 460-480 (1996); http://blastwustl/edu/blast/README.html]. WU-BLAST-2 uses several search parameters, most of which are set to the default values. The adjustable parameters are set with the following values: overlap span=1, overlap fraction=0.125, word threshold (T)=11. The HSP S and HSP S2 parameters are dynamic values and are established by the program itself depending upon the composition of the particular sequence and composition of the particular database against which the sequence of interest is being searched; however, the values may be adjusted to increase sensitivity. A % amino acid sequence identity value is determined by the number of matching identical residues divided by the total number of residues of the "longer" sequence in the aligned region. The "longer" sequence is the one having the most actual residues in the aligned region (gaps introduced by WU-Blast-2 to maximize the alignment score are ignored).

An updated BLAST algorithm, is described in Altschul, et al., *Nucleic Acid Res.* 25, 3389-3402 (1997). A particularly useful BLAST program is Basic BLAST. Preferred parameters are Lambda K H 0.318, 0.135, 0.401 and gapped Lambda K H 0.27, 0.0470, 0.23, Matrix: BLOSUM62, gap penalties: existence 11, extension 1. Preferred parameters for the multiple alignments shown herein which were done on the Lasergene program suite from DNASTAR are the default parameters of the Clustal algorithm in the Megalign program. The parameter information is: (multiple alignments) gap penalty 10, gap length penalty 10, (pairwise alignments) ktuple 1, gap penalty 3, window 5 and diagonals 5.

Thus, "percent (%) nucleic acid sequence identity" is defined as the percentage of nucleotide residues in a candidate sequence that are identical with the nucleotide residues of the sequence shown in the nucleic acid figures. A preferred method utilizes the BLASTN module of WU-BLAST-2 set to the default parameters, with overlap span and overlap fraction set to 1 and 0.125, respectively.

The alignment may include the introduction of gaps in the sequences to be aligned. A particularly preferred method uses the BLASTX and BLASTP modules of Basic BLAST set to matrix BLOSUM62 and a gap penalty of 11 for existence and a gap penalty of 1 for extension.

In addition, for sequences which contain either more or fewer nucleosides than those of the nucleic acid figures, it is understood that the percentage of homology will be determined based on the number of homologous nucleosides in relation to the total number of nucleosides. Thus, for example, homology of sequences shorter than those of the sequences identified herein and as discussed below, will be determined using the number of nucleosides in the shorter sequence.

In one embodiment, the DKGR nucleic acid is determined through hybridization studies. Thus, for example, nucleic acids which hybridize under high stringency to the nucleic acid sequences identified in the figures, or a complement, are considered DKGR sequence in one embodiment herein. High stringency conditions are known in the art; see for example Maniatis, et al., *Molecular Cloning: A Laboratory Manual*, 2d Edition (1989), and *Short Protocols in Molecular Biology*, ed. Ausubel, et al., both of which are hereby incorporated by reference. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Acid Probes*, "Overview of principles of hybridization and the strategy of nucleic acid assays" (1993). Generally, stringent conditions are selected to be about 5-10° C. lower than the thermal melting point (Tm) for the specific sequence at a defined ionic strength pH. The Tm is the temperature (under defined ionic strength, pH and nucleic acid concentration) at which 50% of the probes complementary to the target hybridize to the target sequence at equilibrium (as the target sequences are present in excess, at Tm, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g. 10 to 50 nucleotides) and at least about 60° C. for long probes (e.g. greater than 50 nucleotides). Stringent conditions may also be achieved with the addition of destabilizing agents such as formamide.

In another embodiment, less stringent hybridization conditions are used; for example, moderate or low stringency conditions may be used, as are known in the art; see Maniatis and Ausubel, supra, and Tijssen, supra.

In addition, in one embodiment the DKGR nucleic acid sequences of the invention are fragments of larger genes, i.e. they are nucleic acid segments. "Genes" in this context includes coding regions, non-coding regions, and mixtures of coding and non-coding regions. Accordingly, as will be appreciated by those in the art, using the sequences provided herein, additional sequences of 2,5-diketo-D-gluconic acid reductase genes can be obtained, using techniques well known in the art for cloning either longer sequences or the full length sequences; see Maniatis et al., and Ausubel, et al., supra, hereby expressly incorporated by reference.

In a preferred embodiment, DKGR sequences are isolated from the environment. By "isolation of environmental DNA" herein is meant extracting soil and/or water samples for genomic DNA. That is, environmental DNA, is DNA obtained from uncultured organisms that have not yet been grown under laboratory conditions.

While it is preferred that DKGR sequences are isolated from uncultured organisms, sequences from cultured organisms may be useful. By "cultured" herein is meant organisms capable of growing in nutrient media in a laboratory. Thus, in alternative embodiments, other sequences are provided from microorganisms capable of converting 2,5-diketo-D-gluconic acid into 2-keto-L-gluconic acid, including the coryneform group of bacteria (*Corynebacterium, Brevibacterium* and *Arthobacter*), as well as species of *Micrococcus, Staphylococcus, Pseudomonas, Bacillus*, and *Citrobacter*. Other microorganisms that have homologues include *N. Crassa, Y. pestis, Zymomonas mobilis, Saccharomyces cerevisiae*.

In another embodiment, the sequences are sequence variants as further described herein.

Once a DKGR nucleic acid sequence is identified, it can be cloned and its constituent parts recombined to form the entire DKGR nucleic acid, or vice versa, a fragment may be formed. Once isolated from its natural source, e.g., contained within a plasmid or other vector or excised therefrom as a linear nucleic acid segment, the recombinant DKGR nucleic acid can be further-used as a probe to identify and isolate other DKGR nucleic acids. It can also be used as a "precursor" nucleic acid to make modified or variant DKGR nucleic acids and proteins. "Recombinant" as used herein refers to a nucleic acid or protein which is not in its native state. For example, the nucleic acid can be genetically engineered, isolated, inserted into a man-made vector or be in a cell wherein it is not natively expressed in order to be considered recombinant.

The term "nucleic acid" refers to deoxyribonucleotides or ribonucleotides and polymers thereof in either single- or double-stranded form. Unless specifically limited, the term encompasses nucleic acids containing known analogues of natural nucleotides which have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions) and complementary sequences and as well as the sequence explicitly indicated. Specifically, degenerate codon substitutions may be achieved by generating sequences in which the third position of one or more selected (or all) codons is substituted with mixed-base and/or deoxyinosine residues (Batzer, et al., *Nucleic Acid Res.* 19:5081 (1991); Ohtsuka, et al., *J. Biol. Chem.* 260: 2605-2608 (1985); Cassol, et al., 1992; Rossolini, et al., *Mol. Cell. Probes* 8:91-98 (1994)). The term nucleic acid is used interchangeably with gene, cDNA, and mRNA encoded by a gene.

The DKGR nucleic acids of the present invention are used in several ways. In a preferred embodiment, nucleic acids encoding DKGR proteins are used to make a variety of expression vectors to express DKGR proteins which can then be used to convert 2,5-diketo-D-gluconic acid to 2-keto-L-gulonic acid, as described below. The expression vectors may be either self-replicating extrachromosomal vectors or vectors which integrate into a host genome. Generally, these expression vectors include transcriptional and translational regulatory nucleic acid operably linked to the nucleic acid encoding the DKGR protein. The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice. The transcriptional and translational regulatory nucleic acid will generally be appropriate to the host cell used to express the DKGR protein; for example, transcriptional and translational regulatory nucleic acid sequences from *Pantoea* are preferably used to express the DKGR protein in *Pantoea*. Numerous types of appropriate expression vectors, and suitable regulatory sequences are known in the art for a variety of host cells.

In general, the transcriptional and translational regulatory sequences may include, but are not limited to, promoter sequences, ribosomal binding sites, transcriptional start and stop sequences, translational start and stop sequences, and enhancer or activator sequences. In a preferred embodiment, the regulatory sequences include a promoter and transcriptional start and stop sequences.

Promoter sequences encode either constitutive or inducible promoters. The promoters may be either naturally occurring promoters or hybrid promoters. Hybrid promoters, which combine elements of more than one promoter, are also known in the art, and are useful in the present invention.

In addition, the expression vector may comprise additional elements. For example, the expression vector may have two replication systems, thus allowing it to be maintained in two organisms, for example in mammalian or insect cells for expression and in a procaryotic host for cloning and amplification. Furthermore, for integrating expression vectors, the expression vector contains at least one sequence homologous to the host cell genome, and preferably two homologous sequences which flank the expression construct. The integrating vector may be directed to a specific locus in the host cell by selecting the appropriate homologous sequence for inclusion in the vector. Constructs for integrating vectors are well known in the art.

In addition, in a preferred embodiment, the expression vector contains a selectable marker gene to allow the selection of transformed host cells. Selection genes are well known in the art and will vary with the host cell used.

The DKGR proteins of the present invention can be produced by culturing a host cell transformed with an expression vector containing nucleic acid encoding a DKGR protein, under the appropriate conditions to induce or cause expression of the DKGR protein. The conditions appropriate for DKGR protein expression will vary with the choice of the expression vector and the host cell, and will be easily ascertained by one skilled in the art through routine experimentation. For example, the use of constitutive promoters in the expression vector will require optimizing the growth and proliferation of the host cell, while the use of an inducible promoter requires the appropriate growth conditions for induction. In addition, in some embodiments, the timing of the harvest is important. For example, the baculoviral systems used in insect cell expression are lytic viruses, and thus harvest time selection can be crucial for product yield.

Appropriate host cells include yeast, bacteria, archaebacteria, fungi, insect and animal cells, including mammalian cells. Of particular interest are *Drosophila melangaster* cells, *Saccharomyces cerevisiae* and other yeasts, *E. coli, Bacillus subtilis, Panteoa* sp., Sf9 cells, C129 cells, 293 cells, *Neurospora*, BHK, CHO, COS, HeLA cells, adenovirus and plant cells. *Pantoea agglomerans*, e.g., strain ATCC 27155; *Pantoea ananatis*, e.g., ATCC 33244, *Pantoea citrea*, e.g., ATCC 31623, *Pantoea dispersa*, e.g., ATCC 14589, *Pantoea punctata*, e.g., ATCC 31626, *Pantoea stewartii*, e.g., ATCC 8199. The selection of the host cell is deemed to be within the scope of those skilled in the art from the teachings herein.

In one embodiment, the DKGR proteins are expressed in mammalian cells. Mammalian expression systems are also known in the art, and include retroviral systems. The methods of introducing exogenous nucleic acid into mammalian hosts, as well as other hosts, is well known in the art, and will vary with the host cell used.

In another embodiment, DKGR proteins are expressed in bacterial systems. Bacterial expression systems are well known in the art. Promoters from bacteriophage may also be used and are known in the art. In addition, synthetic promoters and hybrid promoters are also useful; for example, the tac promoter is a hybrid of the trp and lac promoter sequences. Furthermore, a bacterial promoter can include naturally occurring promoters of non-bacterial origin that have the ability to bind bacterial RNA polymerase and initiate transcription. In addition to a functioning promoter sequence, an efficient ribosome binding site is desirable. The expression vector may also include a signal peptide sequence that provides for secretion of the DKGR protein in bacteria. The protein is either secreted into the growth media (gram-positive bacteria) or into the periplasmic space, located between the inner and outer membrane of the cell (gram-negative bacteria). The expression vector may also include an epitope tag providing for affinity purification of the DKGR protein. The bacterial expression vector may also include a selectable marker gene to allow for the selection of bacterial strains that have been transformed. Suitable selection genes include genes which render the bacteria resistant to drugs such as ampicillin, chloramphenicol, erythromycin, kanamycin, neomycin and tetracycline. Selectable markers also include biosynthetic genes, such as those in the histidine, tryptophan and leucine biosynthetic pathways. These components are assembled into expression vectors. Expression vectors for bacteria are well known in the art, and include vectors for *Bacillus subtilis, E. coli, Streptococcus cremoris*, and *Streptococcus lividans*, among others. The bacterial expression vectors are transformed into bacterial host cells using techniques well known in the art, such as calcium chloride treatment, electroporation, and others. Preferably, expression vectors are used for *Pantoea* sp., for example, as demonstrated below in the examples.

In one embodiment, DKGR proteins are produced in insect cells. Expression vectors for the transformation of insect cells, and in particular, baculovirus-based expression vectors, are well known in the art.

In another embodiment, DKGR proteins are produced in yeast cells. Yeast expression systems are well known in the art, and include expression vectors for *Saccharomyces cerevisiae, Candida albicans* and *C. maltosa, Hansenula polymorpha, Kluyveromyces fragilis* and *K. lactis, Pichia guillerimondii* and *P. pastoris, Schizosaccharomyces pombe*, and *Yarrowia lipolytica*.

Accordingly, the present invention also provides DKGR protein sequences. A DKGR protein of the present invention may be identified in several ways. "Protein" in this sense includes proteins, polypeptides, enzymes and peptides. As will be appreciated by those in the art, the nucleic acid sequences of the invention can be used to generate protein sequences. In particular, full length sequences and homologs can be identified by the sequences or fragments thereof provided herein. It is also understood that naturally occurring allelic variants of the sequences provided herein are further provided herein.

Also included within one embodiment of DKGR proteins are amino acid variants of the naturally occurring sequences, as determined herein. Preferably, the variants are preferably greater than about 55%, 60% or 70% homologous to the wild-type sequence, more preferably greater than about 70% or 80%, even more preferably greater than about 85% and most preferably greater than 90%. In some embodiments the homology will be as high as about 93 to 95 or 98%. As for nucleic acids, homology in this context means sequence similarity or identity, with identity being preferred. This homology will be determined using standard techniques known in the art as are outlined above for the nucleic acid homologies. The proteins of the present invention may be shorter or longer than the wild type amino acid sequences. Thus, in a preferred embodiment, included within the definition of DKGR proteins are portions or fragments of the wild type sequences.

In one embodiment, a fragment has or encodes a protein which has a binding domain to a modulating agent, energy source, substrate or antibody.

Preferred fragments comprise the N-terminal domain which is defined herein as containing about 100 amino acids beginning with the start methionine as standard in the art. In another embodiment, a peptide consisting essentially of the N-terminal domain is provided. Preferably, the N-terminal domain comprises hydrophobic side chains that point into a common center of the N-terminal domain. For example, see, residues 37, 44, 60 and 70 or corresponding residues of the DKGRd described below in the examples. Preferably, the N-terminal domain of a DKGR provides thermal stability.

In another embodiment, a fragment provided herein comprises the C-terminal domain which is defined herein as containing about 100 amino acids ending at the carboxyl end of the full length protein. In another embodiment, a peptide consisting essentially of the C-terminal domain is provided. Preferably, the C-terminal domain of a DKGR provides for substrate specificity, and more preferably, for improved specificity over previously known reductases.

In addition, as outlined above, the DKGR nucleic acids of the invention may be used to obtain additional coding and non-coding regions, and thus in the case of coding regions, additional protein sequence, using techniques known in the art.

In preferred embodiment, the DKGR protein is DKGRc (pI-14) or DKGRd (pI-28) as shown in the FIGS. 2 and 3, or a fragment thereof. For simplicity, at times herein DKGR is discussed in an exemplary manner, however, it is understood that in some embodiments, particularly in the methods described herein, different embodiments of the DKGR proteins as described herein may be used.

In one embodiment, the DKGR proteins are derivative or variant DKGR proteins as compared to the wild-type sequence. That is, as outlined more fully below, the derivative DKGR peptide will contain at least one amino acid substitution, deletion, insertion, or combination thereof, with amino acid substitutions being particularly preferred. The amino acid substitution, insertion or deletion or combination thereof may occur at any residue within and/or at a terminal end of the DKGR peptide. These variants ordinarily are prepared by site specific mutagenesis of nucleotides in the DNA encoding the DKGR protein, using cassette or PCR mutagenesis or other techniques well known in the art, to produce DNA encoding the variant, and thereafter expressing the DNA in recombinant cell culture as outlined above. However, variant DKGR protein fragments having up to about 100-150 residues may be prepared by in vitro synthesis using established techniques. Amino acid sequence variants are characterized by the predetermined nature of the variation, a feature that sets them apart from naturally occurring allelic or interspecies variation of the DKGR protein amino acid sequence. The variants typically exhibit the same qualitative biological activity as the naturally occurring analogue, although variants can also be selected which have modified characteristics as will be more fully outlined below.

While the site or region for introducing an amino acid sequence variation is predetermined, the mutation per se need not be predetermined. For example, in order to optimize the performance of a mutation at a given site, random mutagenesis may be conducted at the target codon or region and the expressed DKGR variants screened for the optimal combination of desired activity. Techniques for making substitution mutations at predetermined sites in DNA having a known sequence are well known, for example, M13 primer mutagenesis and PCR mutagenesis. Screening of the mutants is done using assays of DKGR protein activities.

Amino acid substitutions are typically of single residues; insertions usually will be on the order of from about 1 to 20 amino acids, although considerably larger insertions may be tolerated. Deletions range from about 1 to about 20 residues, although in some cases deletions may be much larger.

Substitutions, deletions, insertions or any combination thereof may be used to arrive at a final derivative. Generally these changes are done on a few amino acids to minimize the alteration of the molecule. However, larger changes may be tolerated in certain circumstances. When small alterations in the characteristics of the DKGR protein are desired, substitutions are generally made in accordance with the following chart:

CHART 1

| Original Residue | Exemplary Substitutions |
| --- | --- |
| Ala | Ser |
| Arg | Lys, His |
| Asn | Gln, His |
| Asp | Glu |
| Cys | Ser |
| Gln | Asn |
| Glu | Asp |
| Gly | Pro |
| His | Asn, Gln |
| Ile | Leu, Val |
| Leu | Ile, Val |
| Lys | Arg, Gln, Glu, Gly |
| Met | Leu, Ile |
| PheSer | Met, Leu, Tyr |
| Thr | Thr |
| Trp | Ser |
| Tyr | Tyr |
| Val | Trp, Phe |
|  | Ile, Leu |

Substantial changes in function or immunological identity are made by selecting substitutions that are less conservative than those shown in Chart I. For example, substitutions may be made which more significantly affect: the structure of the polypeptide backbone in the area of the alteration, for example the alpha-helical or beta-sheet structure; the charge or hydrophobicity of the molecule at the target site; or the bulk of the side chain. The substitutions which in general are expected to produce the greatest changes in the polypeptide's properties are those in which (a) a hydrophilic residue, e.g. seryl or threonyl is substituted for (or by) a hydrophobic residue, e.g. leucyl, isoleucyl, phenylalanyl, valyl or alanyl; (b) a cysteine or proline is substituted for (or by) any other residue; (c) a residue having an electropositive side chain, e.g. lysyl, arginyl, or histidyl, is substituted for (or by) an electronegative residue, e.g. glutamyl or aspartyl; or (d) a residue having a bulky side chain, e.g. phenylalanine, is substituted for (or by) one not having a side chain, e.g. glycine.

The variants typically exhibit the same qualitative biological activity and will elicit the same immune response as the naturally-occurring analogue, although variants also are selected to modify the characteristics of the DKGR proteins as needed. Alternatively, the variant may be designed such that the biological activity of the DKGR protein is altered.

Covalent modifications of DKGR polypeptides are included within the scope of this invention. One type of covalent modification includes reacting targeted amino acid residues of a DKGR polypeptide with an organic derivatizing agent that is capable of reacting with selected side chains or the N- or C-terminal residues of a DKGR polypeptide. Derivatization with bifunctional agents is useful, for instance, for crosslinking DKGR protein to a water-insoluble support matrix or surface for use in the method for purifying anti-DKGR antibodies or screening assays, as is more fully described below. Commonly used crosslinking agents include, e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidylpropionate), bifunctional maleimides such as bis-N-maleimido-1,8-octane and agents such as methyl-3-[(p-azidophenyl)dithio]pro-pioimidate.

Other modifications include deamidation of glutaminyl and asparaginyl residues to the corresponding glutamyl and aspartyl residues, respectively, hydroxylation of proline and lysine, phosphorylation of hydroxyl groups of seryl, threonyl or tyrosyl residues, methylation of the α-amino groups of lysine, arginine, and histidine side chains [T. E. Creighton, Proteins: Structure and Molecular Properties, W.H. Freeman & Co., San Francisco, pp. 79-86 (1983)], acetylation of the N-terminal amine, and amidation of any C-terminal carboxyl group.

Another type of covalent modification of the DKGR polypeptide included within the scope of this invention comprises altering the native glycosylation pattern of the polypeptide. "Altering the native glycosylation pattern" is intended for purposes herein to mean deleting one or more carbohydrate moieties found in native sequence DKGR polypeptide, and/or adding one or more glycosylation sites that are not present in the native sequence DKGR polypeptide.

Addition of glycosylation sites to DKGR polypeptides may be accomplished by altering the amino acid sequence thereof. The alteration may be made, for example, by the addition of, or substitution by, one or more serine or threonine residues to the native sequence DKGR polypeptide (for O-linked glycosylation sites). The DKGR amino acid sequence may optionally be altered through changes at the DNA level, particularly by mutating the DNA encoding the DKGR polypeptide at preselected bases such that codons are generated that will translate into the desired amino acids.

Another means of increasing the number of carbohydrate moieties on the DKGR polypeptide is by chemical or enzymatic coupling of glycosides to the polypeptide. Such methods are described in the art, e.g., in WO 87/05330 published 11 Sep. 1987, and in Aplin and Wriston, Crit. Rev. Biochem. pp. 259-306 (1981).

Removal of carbohydrate moieties present on the DKGR polypeptide may be accomplished chemically or enzymatically or by mutational substitution of codons encoding for amino acid residues that serve as targets for glycosylation. Chemical deglycosylation techniques are known in the art and described, for instance, by Hakimuddin, et al., Arch. Biochem. Biophys. 259:52 (1987) and by Edge, et al., Anal. Biochem. 118:131 (1981). Enzymatic cleavage of carbohydrate moieties on polypeptides can be achieved by the use of a variety of endo- and exo-glycosidases as described by Thotakura, et al., Meth. Enzymol. 138:350 (1987). Preferably, the DKGR protein is non-glycosylated. For example, in one embodiment the protein is, for example, human, expressed in bacteria, for example, E. coli. Moreover, phosphorylation and/or methylation of DKGR as used herein may differ from DKGR as found in its native form within a cell.

Another type of covalent modification of DKGR comprises linking the DKGR polypeptide to one of a variety of nonproteinaceous polymers, e.g., polyethylene glycol, polypropylene glycol, or polyoxyalkylenes, in the manner set forth in U.S. Pat. Nos. 4,640,835; 4,496,689; 4,301,144; 4,670,417; 4,791,192 or 4,179,337.

The DKGR polypeptides of the present invention may also be modified in one embodiment in a way to form chimeric molecules comprising a DKGR polypeptide fused to another, heterologous polypeptide or amino acid sequence. In one embodiment, such a chimeric molecule comprises a fusion of a DKGR polypeptide with a tag polypeptide which provides an epitope to which an anti-tag antibody can selectively bind. Preferred tags include the myc epitope and 6-histidine. The epitope tag is generally placed at the amino- or carboxyl-terminus of the DKGR polypeptide. The presence of such epitope-tagged forms of a DKGR polypeptide can be detected using an antibody against the tag polypeptide as further discussed below. Also, provision of the epitope tag enables the DKGR polypeptide to be readily purified by affinity purification using an anti-tag antibody or another type of affinity matrix that binds to the epitope tag. In an alternative embodiment, the chimeric molecule may comprise a fusion of a DKGR polypeptide with an immunoglobulin or a particular region of an immunoglobulin. For a bivalent form of the chimeric molecule, such a fusion could be to the Fc region of an IgG molecule.

Various tag polypeptides and their respective antibodies are well known in the art. Examples include poly-histidine (poly-his) or poly-histidine-glycine (poly-his-gly) tags; the flu HA tag polypeptide and its antibody 12CA5 (Field, et al., Mol. Cell. Biol. 8:2159-2165 (1988)); the c-myc tag and the 8F9, 3C7, 6E10, G4, B7 and 9E10 antibodies thereto (Evan, et al., Molecular and Cellular Biology 5:3610-3616 (1985)); and the Herpes Simplex virus glycoprotein D (gD) tag and its antibody (Paborsky, et al., Protein Engineering 3(6):547-553 (1990)). Other tag polypeptides include the Flag-peptide (Hopp, et al., BioTechnology 6:1204-1210 (1988)); the KT3 epitope peptide (Martin, et al., Science 255:192-194 (1992)); tubulin epitope peptide (Skinner, et al., J. Biol. Chem. 266: 15163-15166 (1991)); and the T7 gene 10 protein peptide tag (Lutz-Freyermuth, et al., Proc. Natl. Acad. Sci. USA 87:6393-6397 (1990)).

Also included with the definition of DKGR protein in one embodiment are other reductase proteins of the aldo-keto reductase superfamily, and DKGR proteins from other organisms, which are cloned and expressed as outlined below. Thus, probe or degenerate polymerase chain reaction (PCR) primer sequences may be used to find other related DKGR proteins from humans or other organisms. As will be appreciated by those in the art, particularly useful probe and/or PCR primer sequences include the unique areas of the DKGR nucleic acid sequence. As is generally known in the art, preferred PCR primers are from about 15 to about 35 nucleotides in length, with from about 20 to about 30 being preferred, and may contain inosine as needed. The conditions for the PCR reaction are well known in the art.

In addition, as is outlined herein, DKGR proteins can be made that are longer than those depicted in the Figures, for example, by the elucidation of additional sequences, the addition of epitope or purification tags, the addition of other fusion sequences, etc.

DKGR proteins may also be identified as being encoded by DKGR nucleic acids. Thus, in one embodiment, DKGR proteins are encoded by nucleic acids that will hybridize to the sequences of the nucleic acid Figures, or their complements, or have homology to or the activity of another DKGR protein as outlined herein.

In a preferred embodiment, the DKGR protein is purified or isolated after expression. DKGR proteins may be isolated or purified in a variety of ways known to those skilled in the art depending on what other components are present in the sample. Standard purification methods include electrophoretic, molecular, immunological and chromatographic techniques, including ion exchange, hydrophobic, affinity, and HPLC chromatography, and chromatofocusing. For example, the DKGR protein may be purified using a standard affinity chromatography followed by ion exchange chromatography.

Ultrafiltration and diafiltration techniques, in conjunction with protein concentration, are also useful. For general guidance in suitable purification techniques, see Scopes, R., Protein Purification, Springer-Verlag, NY (1982). The degree of purification necessary will vary depending on the use of the DKGR protein. In some instances, no purification will be necessary.

The terms "isolated" "purified" or "biologically pure" refer to material that is substantially or essentially free from components which normally accompany it as found in its native state. Purity and homogeneity are typically determined using analytical chemistry techniques such as polyacrylamide gel electrophoresis or high performance liquid chromatography. A protein that is the predominant species present in a preparation is substantially purified. The term "purified" denotes that a nucleic acid or protein gives rise to essentially one band in an electrophoretic gel. Particularly, it means that the nucleic acid or protein is at least 85% pure, more preferably at least 95% pure, and most preferably at least 99% pure. In a preferred embodiment, a protein is considered pure wherein it is determined that there is no contaminating activity.

Once expressed and purified if necessary, the DKGR proteins and nucleic acids are useful in a number of applications. For example, DKGR nucleic acids may be sequenced and subjected to site specific mutagenesis to develop modified DKG reductases with desired properties that are absent or less pronounced in the wild-type proteins, such as stability to heat, solvent tolerance, NADH dependent activity and different pH optimum.

The DKGR nucleic acids and proteins of this invention may be employed for any purpose in which DKGR enzyme activity is necessary or desired. In a preferred embodiment, DKGR nucleic acids and proteins are used to make enzymes useful in industrial processes.

In a preferred embodiment, DKGR nucleic acids and proteins are used to make enzymes which can be used commercially to convert glucose to vitamin C in a single organism. In this process, a strain capable of converting glucose to 2,5-diketo-D-gluconic acid via an endogenous oxidase is engineered to express a DKG reductase obtained using one of the methods of the present invention. The strain has a source for glucose or making glucose or is provided with one. The resulting recombinant strain then converts glucose to 2-keto-L-gulonic acid in a single fermentation step.

In one embodiment, a microorganism capable of direct production of 2-keto-L-gulonate from D-glucose is provided. In one embodiment, the gulonate is subsequently converted into vitamin C.

The DKGR proteins, their fragments or other derivatives, or analogs thereof can be used as an immunogen to produce antibodies. These antibodies can be polyclonal or monoclonal.

In one embodiment, the term "antibody" includes antibody fragments, as are known in the art, including Fab, $Fab_2$, single chain antibodies (Fv for example), chimeric antibodies, etc., either produced by the modification of whole antibodies or those synthesized de novo using recombinant DNA technologies.

Methods of preparing polyclonal antibodies are known to the skilled artisan. Polyclonal antibodies can be raised in a mammal, for example, by one or more injections of an immunizing agent and, if desired, an adjuvant. Typically, the immunizing agent and/or adjuvant will be injected in the mammal by multiple subcutaneous or intraperitoneal injections. The immunizing agent may include the DKGR protein, fragment thereof, or a fusion protein thereof. It may be useful to conjugate the immunizing agent to a protein known to be immunogenic in the mammal being immunized. Examples of such immunogenic proteins include but are not limited to keyhole limpet hemocyanin, serum albumin, bovine thyroglobulin, and soybean trypsin inhibitor. Examples of adjuvants which may be employed include Freund's complete adjuvant and MPL-TDM adjuvant (monophosphoryl Lipid a, synthetic trehalose dicorynomycolate). The immunization protocol may be selected by one skilled in the art without undue experimentation.

The antibodies may, alternatively, be monoclonal antibodies. Monoclonal antibodies may be prepared using hybridoma methods, such as those described by Kohler and Milstein, Nature, 256:495 (1975). In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes may be immunized in vitro. The immunizing agent will typically include the DKGR polypeptide or fragment thereof or a fusion protein thereof. Generally, either peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell (Goding, Monoclonal Antibodies: Principles and Practice, Academic Press pp. 59-103). Immortalized cell lines are usually transformed mammalian cells, particularly myeloma cells of rodent, bovine and human origin. Usually, rat or mouse myeloma cell lines are employed. The hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Antibodies generated against the DKGR proteins of the present invention may be used in screening for similar enzymes from other organisms and samples. Antibodies may also be employed as proves to screen gene libraries to identify DKG reductases or cross reactive activities.

The following examples serve to more fully describe the manner of using the above-described invention, as well as to set forth the best modes contemplated for carrying out various aspects of the invention. It is understood that these examples in no way serve to limit the true scope of this invention, but rather are presented for illustrative purposes. All references cited herein are incorporated by reference.

EXAMPLES

Example 1

Isolation of Environmental 2,5-diketo-D-gluconic acid reductases, DKGRc and DKGRd Materials and Methods:

Extraction and purification of DNA from soil and water sediment samples was done as described previously (Eschenfeldt, et al., *Isolation of a full-length hsp60 gene from environmental DNA by polymerase chain reaction* (2000)). Water and soil samples were collected in the summer of 1996 from a pond, a deciduous forest and near the base of a cultivated berberry bush in the vicinity of Argonne National Laboratory, Argonne, Ill.

Pond water was collected in plastic carboys and the suspended matter was concentrated either by flow-through centrifugation (Sharples, model A5-16) or, for small volumes, by filtration through 0.22 μm nitrocellulose filters. The DNA was extracted from the concentrates using a commercial genomic DNA extraction kit (Puregene) following the methods described by the manufacturer.

Soil samples were collected after removing surface debris and scraping away about 3 cm of topsoil. Samples from 3 to 6 cm below the surface were placed in sterile sealable plastic bags returned to the laboratory and stored at 4° C. until DNA extraction. The extraction procedure was essentially as described by (Selenska, S, and W. Klingmüller, *Lett. Appl. Microbiol.* 13(1):21-24 (1991)). Two grams (wet weight) of soil were suspended in 4 ml of extraction buffer (120 mM $Na_2HPO_4$ (pH 8.0) and 1% sodium dodecyl sulfate). The suspension was shaken at 200 rpm for 1 hr at 70° C. in a New Brunswick shaker incubator and then centrifuged at 3000×g for 5 min. at room temperature in a table top centrifuge. The DNA-containing supernatant was collected and the soil pellet was extracted two additional times by resuspending it in 2 ml of extraction buffer, shaking for 20 min. at 70° C., and centrifuging as before. The combined supernatants were centrifuged at 20,000×g for 10 min. at room temperature to remove residual particles. These samples were stored at 4° C. until further processing.

The humic substances were removed from soil extracts by size exclusion chromatography (Sepharose CL-4B) followed by ion exchange chromatography (Tip 500G; Qiagen). For the Sepharose separation 150 μl glycerol was added to 1.4 ml of the soil DNA extract and the sample applied to the surface of a 1.0×20 cm CL-4B column equilibrated in 10 mM Tris (7.5), 1 mM EDTA, 100 mM NaCl (TEN). The void-volume fractions containing the DNA were pooled and ethanol precipitated. (The column could be reused by thorough washing with TEN buffer). Precipitated DNA was dissolved in 10 mM Tris (pH 8.4) and NaCl was added to a final concentration of 0.75 M. The DNA was further purified using a Qiagen Tip 500G column according to the manufacturer's instructions. The isopropanol-precipitated DNA recovered from the Tip 500G column was dissolved in 500 μl 10 mM Tris (pH 8.0), its concentration determined by absorbance at 260 nm, and stored at −20° C.

Internal fragments of genes were amplified using degenerate primers. Degenerate primers were designed based on sequence comparisons of the two known 2,5DKG reductase genes from *Corynebacterium* [Genbank Accession M12799 (Anderson, et al., *Science* 230:144-149 (1985)) and M21193 (Grindley, et al., *Appl. Environ. Microbiol.* 54(7):1770-1775 (1988))] and what appeared to be the closely related morphine dehydrogenase gene from *Pseudomonas putida* [GB: M94775 (Willey, et al., *Biochem. J.* 290 (Pt 2):539-544 (1993)]. The amino acid sequences of these three genes were aligned using the Clustal method (Megalign program, DNA Star). Two primers of 20 nucleotides were designed based on regions of identity or strong similarity for at least seven amino acids. The primers were analyzed for hairpin and duplex formation, predicted melting temperature, and free energy of association with the Oligo 5 program (National Biosciences, Inc.). The two oligonucleotides, designated DU1 and DL1 were synthesized by the HHMI/Keck Oligonucleotide Synthesis Facility, Yale University.

Optimal conditions for PCR with the degenerate primers were determined using the plasmid ptrpl-35a (Anderson, et al., *Science* 230:144-149 (1985)) containing the *Corynebacterium* 2,5DKGa reductase gene. Unless stated otherwise, all PCR reactions (50 μl reaction volume) contained 1× Mg-free buffer, 200 μM each of the four dNTPs, 2.5 mM $MgCl_2$, 2 μM each of the degenerate primers, 1.5 units Taq polymerase (Promega), and 25-100 ng environmental DNA prepared as described above. PCR conditions began with 94° C. (1 min) followed by 40 cycles of 94° C. (30 sec), 58° C. (45 sec), and 72° C. (1 min), and ending with an incubation at 72° C. for 60 min. PCR products were analyzed by electrophoresis in a 1% agarose gel as described elsewhere (Sambrook, et al., *Molecular Cloning: A Laboratory Manual*. Cold Spring Harbor Laboratory Press, Cold Spring, Harbor, N.Y. (1989)).

The PCR product was purified by electrophoresis in 1.0% agarose gels in TBE buffer. The band of interest was excised from the gel and the DNA extracted with the QiaQuick gel purification kit (Qiagen) following the manufacturer's instructions. The purified DNA was ligated into the vector pBluescript SK+ (Stratagene) digested with EcoRV (Promega) and a single T residue added at the 3' ends by tailing with dTTP and Taq polymerase (Ausubel, et al., *Current Protocols in Molecular Biology*. John Wiley and Sons, Inc., New York (1988)) T4 DNA ligase and 10× buffer were obtained from Promega and used according to the manufacturer's instructions. Ligated DNA was transformed into *Escherichia coli* DH5a (MaxEfficiency, GIBCO/BRL) according to the manufacturer's instructions. *E. coli* was cultured on LB agar plates containing ampicillin, IPTG, and Xgal. (Sambrook, et al., *Molecular Cloning: A Laboratory Manual. Cold Spring Harbor Laboratory Press, Cold Spring Harbor, N.Y.* (1989)). White colonies were analyzed for vectors containing DNA inserts of the expected sizes using PCR. The T3 and T7 promoter regions of the vector were used for primers and the PCR was conducted using the conditions described above.

Plasmid clones were sequenced using the ABI Prism Dye Terminator Cycle Sequencing Ready Reaction Kit (Perkin-Elmer Applied Biosystems) in a Perkin-Elmer GeneAmp PCR System 9600 thermocycler using T3 and T7 promoter primers. All component concentrations, incubation and cycling conditions followed the manufacturer's instructions. Samples were separated on a 6% acrylamide gel containing 8M urea in an Applied Biosystems 373A DNA Sequencer (Perkin-Elmer Applied Biosystems) following the manufacturer's instructions. Sequences were analyzed using the Seqman program (DNA Star).

The flanking regions of the genes were amplified as follows. The nucleotide sequences of the cloned environmental PCR fragments were aligned using the Megalign program from DNA Star. Potential clone-specific primers were chosen from areas with the least sequence homology. Primer melting temperature, free energy of association, duplex formation and predicted performance in a PCR reaction were examined using the Oligo 5 program (National Biosciences, Inc.). Optimal conditions for each set of primers were determined experimentally using the specific clone as template. Specificity of the primers was determined by testing each set of primers with each of the environmental clones as template. A primer pair was considered specific if it generated the expected band only with its specific template. The sequences of the clone-specific primers for the two 2,5DKG reductase-related clones selected for further study (pI-14 and pI-28) are shown in Table 1. Contiguous DNA from the 5'- and 3'-flanking regions was obtained by restriction-site PCR.

TABLE 1

PCR Primer Sequences

| Oligo | Sequence | Length |
|---|---|---|
| DU1 | GGCTACCGNCWSMTCGACAC (SEQ ID NO: 11) | 20 |
| DL1 | GGGTGSAGCTCGAYCTGGTT (SEQ ID NO: 12) | 20 |
| 14U1 | CTATGACAATGAGGCAGAGGTC (SEQ ID NO: 13) | 22 |
| 14U2 | CGCGCGCGAGGAAGTTTTTGTGACA (SEQ ID NO: 14) | 25 |
| 14U3 | CCGTGCCCGAAGCAAGACAA (SEQ ID NO: 15) | 20 |
| 14U4 | ACCCCATCTCGAGAAGCTCTTG (SEQ ID NO: 16) | 22 |
| 14U5 | TCATAATTCGCTGGCACCTG (SEQ ID NO: 17) | 20 |
| 14U6 | GCCGTTTTCGCTGTCACCTA (SEQ ID NO: 18) | 20 |
| 14L1 | GCTGCAAGAGCTTCTCGAGATG (SEQ ID NO: 19) | 22 |
| 14L2 | AGTTCGAGACTCCGATGCCCTTAAC (SEQ ID NO: 20) | 25 |
| 14L3 | CGAATGCGTGCCAAGTCTCAA (SEQ ID NO: 21) | 21 |
| 14L4 | GACCTCTGCCTCATTGTCATAG (SEQ ID NO: 22) | 22 |
| 14L5 | CGCCACGAGCCTTGAGTTGT (SEQ ID NO: 23) | 20 |
| 14L6 | TTTCTTCGTCCAGGGGAGTTTG (SEQ ID NO: 24) | 22 |
| 14L7 | GCGTGCCCGGCTGAAGGTAA (SEQ ID NO: 25) | 20 |
| 14expU | GAGAACAATTGTATGAGCGCAGAACAGCCT (SEQ ID NO: 26) | 30 |
| 14expL | TCTTCTAAGCTTCACTAATTCATATCGTCAGGATT (SEQ ID NO: 27) | 35 |
| 28U1 | TTATGACAACGAGGCCGAGGTT (SEQ ID NO: 28) | 22 |
| 28U2 | GCCATTCAAGAGTCGGTCGACA (SEQ ID NO: 29) | 22 |

TABLE 1-continued

PCR Primer Sequences

| Oligo | Sequence | Length |
|---|---|---|
| 28U3 | CGAAACCGGATTGGTGAAATCA (SEQ ID NO: 30) | 22 |
| 28U4 | TTCTTGCGGCTGCGAATGTTGT (SEQ ID NO: 31) | 22 |
| 28U5 | TCGGCCCGTGGAGCCAAAAC (SEQ ID NO: 32) | 20 |
| 28L1 | ACAACATTCGCAGCCGCAAGAA (SEQ ID NO: 33) | 22 |
| 28L2 | GAAAGTTTGAGACACCGATTGAT (SEQ ID NO: 34) | 23 |
| 28L3 | ACCGATTGATTTCACCAATCCG (SEQ ID NO: 35) | 22 |
| 28L4 | TTGCCTCGTGGTATCCGTGGCG (SEQ ID NO: 36) | 22 |
| 28L5 | TACGAAAATCTCTTCGCGGTCT (SEQ ID NO: 37) | 22 |
| 28L6 | AACCTCGGCCTCGTTGTCATAA (SEQ ID NO: 38) | 22 |
| 28L7 | TCGCGCTCTGAATCGTTCTG (SEQ ID NO: 39) | 20 |
| 28expU | GAGAACAATTGTATGGCATCGCCGCTGGTT (SEQ ID NO: 40) | 30 |
| 28expL | TCTTCTAAGCTTCACTAATTCATGTCGTCTGGGTT (SEQ ID NO: 41) | 35 |

Restriction-site PCR (RS-PCR) (Sarkar, et al., *PCR Methods Appl.* 2(4):318-322 (1993)) primers were synthesized by the HHMI/Keck Oligonucleotide Synthesis Facility, Yale University. Primers were of the general structure $N_{10}$GAATTC, where the first 10 positions are completely degenerate and the final six specify a restriction site, EcoRI in the example. Nco I, Pvu II, Xho I, Bgl I and Hind III primers were also used. A series of three semi-nested PCR reactions were performed. For the 3'-flanking region, the first reaction used one of the RS-PCR primers and the appropriate specific primer U1 at 20 μM, 100 ng of environmental DNA, and 1.25 units Taq polymerase (Promega). Samples were denatured at 94° C. for 1 minute followed by 30 cycles at 94° C. (30 sec.), 50° C. (1 min.), and 72° C. (2 min.), with a final incubation at 72° C. for 15 min. Rounds two and three were identical except that 1 μl of the PCR reaction from the previous round was used as template and specific primers U2 and U3 were used in rounds 2 and 3, respectively. Aliquots of each reaction were analyzed by electrophoresis in a 1% agarose gel. Candidate bands were excised from the gel, purified and sequenced directly using clone-specific primers. To obtain the 5'-flanking regions, the appropriate clone-specific primers L1-L3 were used.

Full-length copies of the pI-14 and pI-28 genes were generated from pond water sediment DNA by PCR with primers specific for the 5'- and 3'-noncoding regions of each gene (14U6, 14L6; 28U5,28L7; see Table 1). Conditions were similar to those used for the degenerate primers. Reaction conditions deviated from the standard conditions only in the use of 1.5 mM $MgCl_2$. Samples were denatured at 94° C. for one minute followed by 30 cycles at 94° C. (30 sec), 58° C. (45 sec), and 72° C. (2 minute), with a final incubation at 72° C. for 15 min.

Adaptor primers were designed which would generate a Mun I site immediately upstream of the initiation codon and a Hind III site immediately downstream of the termination codon of each gene. (14expU, 14expL; 28expU, 28expL; see Table 1). The full-length PCR products from the direct amplification were used as template, and the reaction conditions were identical to those described above. The products of these reactions were purified by agarose gel electrophoresis, digested with Mun I and Hind III, and ligated into the expression vector pJF118EH (Fürste, et al., *Gene* 48(1):119-131 (1986)) which had been digested with EcoR I and Hind III. The ligated DNA was transformed into *E. coli* DH5a or JM109 and screened as described above.

Results:

Degenerate primers DU1 and DL1 target highly conserved internal regions of the amino acid sequence of bacterial DKGRs. In a control reaction, using a plasmid bearing the *Corynebacterium* DKGRa gene as template, a well-defined band of the expected 380 bp product was obtained. When various environmental DNA extracts were used as template, agarose gel electrophoresis revealed broad bands between 350 and 400 bp in size. These bands were excised from the gel, ligated into the vector pBluescript SK+ (Promega) and transformed into *E. coli* DH5α. A total of six clones that contained inserts of approximately 350-400 bp were isolated for further study (Table 2). Sequencing revealed that all six clones were different from one another. A BLASTX (Altschul, et al., *Nucleic Acids Res.* 25(17):3389-3402 (1997)) search of the Genbank database indicated that all six were members of the aldo-keto reductase gene family, and none was identical to any sequences in public databases. Alignment of the nucleotide sequences of the clones (FIG. 1) revealed that two, pI-14 and pI-28, were 79% nucleotide sequence identity excluding the primer sequences). These clones possessed 46-48% amino acid sequence identity with the *Corynebacterium* DKGRa gene [GB accession M12799 (Anderson, et al., *Science* 230:144-149 (1985))]. These two clones were chosen for further study.

TABLE 2

Cloned PCR Fragments

| DNA Clone | Source | Insert Size (without primers) | BLASTX Search Results |
|---|---|---|---|
| pI-14 (Kunst, et al., *Nature* 390(6657): 249-256 (1997)) | soil[1] | 340 bp | *B. subtilis* ysvb (Z99121) |
| pI-28 (Kunst, et al., *Nature* 390(6657): 249-256 (1997)) | soil[1] | 340 bp | *B. subtilis* ysvb (Z99121) |
| pII-4 (Kunst, et al., *Nature* 390(6657): 249-256 (1997)) | soil[2] | 331 bp | *B. subtilis* ysvb (Z99121) |
| pIII-6 | pond[3] | 337 bp | *E. coli* yafb (U70214) |
| pIII-19 (Lapidus, et al., *Microbiology* 143(Pt 11): 3431-3441 (1997)) | pond | 370 bp | *B. subtilis* ytbe (AF008220) |
| pIII-24 (Redenbach, et al., *Mol. Microbiol.* 21(l): 77-96 (1996)) | pond | 331 bp | *S. coelicolor* (CAA22355) |

[1]soil surrounding the roots of a berberry bush
[2]soil from a deciduous forest
[3]direct submission The 5' and 3' flanking sequences for clones pI-14 and pI-28 were obtained by restriction-site PCR (RSPCR) (Sarkar, et al., *PCR Methods Appl.* 2(4):318-322 (1993)). Nested, clone-specific primers (Table 1) were designed for both pI-14 and pI-28 and used together with several different RSPCR primers. The initial amplification, using environmental DNA as template, generated a diffuse smear of products with a few, faintly discernible bands. Subsequent rounds of PCR used the product of the previous reaction as template, the same RSPCR primer, and a downstream nested primer. With each round, increasingly discrete products were generated. After three or four rounds, discrete products were formed in good yield. For the of 3' flanking region, an approximately 800 bp fragment was generated with the Xho I RSPCR primer for both the pI-14 and pI-28 clones. Approximately 500 bp fragment of 5' flanking sequence was generated for each clone using the Bgl I RSPCR primer.

Sequencing of the final products confirmed that the flanking regions overlapped with the sequence of the original clones. Putative complete nucleotide sequences for the I-14 and I-28 genes were constructed from the overlapping fragments (FIG. 2). The putative DKG reductase gene in clone pI-14 is predicted to start at the GTG codon at position 312. In clone pI-28 the putative gene begins at the ATG codon at position 94. The deduced amino acid sequences of the predicted reductases were homologous to that of the *Corynebacterium* sps. DKGRa.

Partial open reading frames were found upstream and downstream from the reductase genes. An upstream putative open reading frame (orf1) begins beyond the range of the amplified fragment and covers 104 amino acids in the pI-14 clone. The termination codon of orf1 overlaps the putative GTG start codon of the DKGR gene. The pI-28 sequence contains the final 29 amino acids of orf1, of which 27 are identical to the pI-14 sequence. A BLASTP search of the Genbank database with the pI-14 orf1 amino acid sequence gave only a few hits. The best match was a hypothetical *E. coli* open reading frame [ACC74333 (Blattner, et al., *Science* 277(5331):1453-1474 (1997))] with an identity of 32% over 103 amino acids. A second potential open reading frame (orf2) starts in both clones at a methionine residue just beyond the reductase termination codon and extends beyond the range of the clones. The orf2 sequences are 88% identical to each other over 86 amino acid residues. A BLASTP search of the sequences gave a best match with a hypothetical protein from *Streptomyces coelicolor* [CAB51274 (Redenbach, et al., *Mol. Microbiol.* 21(1):77-96 (1996))] with an identity of 45% over a range of 85 amino acids.

To establish that the assembled pI-14 and pI-28 genes are truly present in the environment and not chimera of multiple homologous genes, we designed specific primers for the 5'- and 3'-noncoding regions of each clone (Table 1). Direct amplification with these primers using the original environmental DNA as template generated products of the predicted size in a single PCR reaction. Sequencing of these bands confirmed their identities as pI-14 and pI-28.

To allow expression of the amplified genes, the coding sequences were cloned into the expression vector pJF118EH (Füurste, et al., *Gene* 48(1):119-131 (1986)). Adaptor-primers were synthesized for clones pI-14 and pI-28 (Table 1). Because the sequences indicated both gene had an internal EcoRI site, the forward primers (14expU and 28expU) added a Mun I restriction site immediately upstream of the initiation codon. For pI-14, the forward primer also changed the 'GTG' initiation codon to ATG. The reverse primers for both clones (14expL, 28expL) added a second, in-frame, termination codon immediately adjacent to the existing termination codon, along with a Hind III restriction site. The full-length PCR products generated from environmental DNA was used as template. The products of these two reactions were cloned into the expression vector pJF118EH and transformed into *E. coli*. Clones with the expected insert sizes were identified and one clone for each gene (designated pI-14 and pI-28, respectively) was selected for further analysis.

The sequences of both clones were determined and the deduced amino acid sequences were compared (FIG. 3). The two clones have an overall amino acid sequence identity of 82.5%. It should be noted that neither of the expression clone sequences were identical to the original clones obtained as RSPCR products. The amino acid sequence of clone pI-14 differed by 4% and clone pI-28 by 1% from their predicted sequences. Such differences may be attributed to the large number of PCR cycles used to generate the original clones.

A search (BLASTP) of the Genbank database for homologues of the pI-14 and pI-28 amino acid sequences indicated that both sequences are most closely related to a putative oxido-reductase gene from *Streptomyces coelicolor* [CAA22355 (Redenbach, et al., *Mol. Microbiol.* 21(1):77-96 (1996)). The homology is 47% identity for PI-14 and 48% identity for PI-28.

Both sequences are also homologous to DKGR of *Corynebacterium* spp with 41% and 42% identity, respectively.

Example 2

Purification of Environmental 2,5-diketo-D-gluconic Acid Reductases, DKGRc and DKGRd Materials and Methods:

Full length environmental 2,5-diketo-D-gluconic acid reductases, DKGRc and DKGRd, were produced by induction of cultures of *E. coli* containing the expression plasmids pI-14 or pI-28. Cultures of *E. coli* DH5α containing pI-14 were grown aerobically at 37° C. in 500 ml of Luria Broth (Sambrook, et al., *Molecular Cloning: A Laboratory Manual*, 2nd ed, vol. 2nd ed. Cold Spring Harbor Press, Cold Spring Harbor, N.Y. (1989)) in a 1 L notched Erlenmeyer flask. Cultures of *E. coli* JM109 containing plasmid pI-28 were grown under the same conditions, but at 30° C. Both cultures were agitated at 250 rpm. When the cultures' $OD_{600}$ reached 0.3-0.5, expression was induced with 1 mM isopropyl-β-D-thiogalactopyranoside (IPTG, U.S. Biochemicals). Cells were harvested after 4 hours (37° C. experiments) or overnight growth (30° C. experiment), washed once with TE buffer, and stored at −70° C. Media components were purchased from Fisher.

For routine enzymatic assays, solid 2,5-diketo-D-gluconic acid (DKG), provided by Genencor International, was used as substrate. For kinetic analyses and for the preparation of the reaction product, DKG was prepared by the oxidation of glucose by permeabilized cells of *Pantoea citrea* and used either without purification to the solid form or with careful drying to prevent hydration of the solid product. *P. citrea* was provided by Genencor International. All other chemicals were from Sigma.

*P. citrea* was grown overnight in 50 ml of Luria Broth containing 20 mM glucose at 28° C. in a notched 250 ml flask at 250 rpm. An additional aliquot of 10 ml of Luria Broth containing 100 mM glucose was added to the culture, and the culture was grown for an additional hour at 28° C. The cells were harvested by centrifugation at 6000 rpm (3600×g) at 20° C. for 10 minutes. The cells were resuspended in 6 ml of 0.1M phosphate buffer, pH 7.2, containing 5 mM $MgCl_2$ and transferred to a stoppered, 125 ml Erlenmeyer flask. The concentration of the cells was adjusted to a final $OD_{600}$ of 10-200D units/ml. The cells were permeabilized by adding 50 μl of a solution of toluene:acetone (1:9) per ml of cells, and vortexing for one minute. To prepare 2,5-diketo-D-gluconic acid, glucose was added to the permeabilized cells to a final concentration of 50 mM, and the cells were incubated at 28° C. for 4-6 hours with agitation at 250 rpm. Cells were removed by centrifugation at 3600×g for 10 minutes, and the supernatant, containing 2,5-diketo-D-gluconic acid, was filtered through a 0.2 micron filter to remove any cell debris. The concentration of 2,5-diketo-D-gluconic acid was determined enzymatically using purified 2,5-diketo-D-gluconic acid reductase. Aliquots of 1 ml were placed at −80° C. for long term storage.

The 2,5-diketo-D-gluconic acid reductases were purified by resuspending cell pellets in approximately 2 volumes of 10 mM Tris/HCl, pH 7.5, containing 1 mM EDTA, 0.5 mM dithiothreitol, and 0.001% phenylmethylsulfonyl fluoride (PMSF). Cells were lysed by passing the suspension twice through a French press. The cell debris and membranes were removed by centrifugation at 950×g followed by ultracentrifugation at 435,000×g in a Beckman TL-100 ultracentrifuge. Both reductases were purified by affinity chromatography on Matrix Red A Gel (Amicon) followed by ion exchange on a MonoQ column (Pharmacia).

A 2×8 cm column of Active Red Matrix was loaded and eluted using a Fast Protein Liquid Chromatography System (Pharmacia Biotech). The column was equilibrated with 10 mM Tris/HCl, pH 7.2, containing 0.5 mM EDTA and 0.5 mM DTT. For form c, approximately 5 ml of ultracentrifuged extract was loaded onto the column at a flow rate of 0.5 ml/min. The column was washed with 40 ml of equilibration buffer at a flow rate of 2 ml/min, then eluted in a stepwise manner, first with 40 ml of equilibration buffer containing 1.5 M NaCl, followed by buffer containing 2.5 M NaCl. The c form reductase eluted in the 2.5 M NaCl wash.

For the form d reductase, this procedure was modified as follows. After loading the enzyme, the column was washed with equilibration buffer, as described above. The enzyme was then eluted with a 100 ml linear gradient from 0-1.5 M NaCl equilibration buffer. The enzyme eluted at a NaCl concentration of approximately 0.6 M. In both purifications, the fractions containing 2,5-diketo-D-gluconic acid reductase activity were pooled and dialyzed against buffer lacking salt.

The pooled, dialyzed fractions were loaded onto a MonoQ HR 10/10 column using a Superloop. The c reductase was eluted using a 2.5%/min linear gradient of 0-1.0 M NaCl in 0.1 M Tris/HCl buffer, pH 7.5, containing 0.5 mM DTT. Purification of the d reductase required two MonoQ steps, performed at pH 7.5 and pH 8.0. The enzyme was eluted from the first column with a 1%/min linear gradients of 0-1.0 M NaCl in 0.1 M Tris/HCl buffer, pH 7.5, containing 0.5 mM DTT. Fractions containing reductase activity were pooled, dialyzed overnight against 100 mM Tris/HCl, pH 8.0, containing 0.5 mM DTT, and loaded onto the MonoQ column which had previously been equilibrated with the same pH 8.0 buffer. The enzyme was eluted with a 1.25%/min linear gradient of 0-1.0 M NaCl in 0.1 M Tris, pH 8.0, containing 0.5 mM DTT. In each case, the 2,5-diketo-D-gluconic acid reductase eluted as a sharp peak (A280) in the final gradient. Purity was evaluated by denaturing gel electrophoresis (Laemmli, *Nature* 227(259):680-685 (1970)).

Results:

DKGRc, which was more highly overexpressed, was quickly purified to homogeneity in two steps. This reductase bound tightly to the affinity column, and was eluted by stepwise increases of the concentration of NaCl. The reductase eluted with 2.5 M NaCl gave sufficiently pure material for purification to homogeneity in a single ion-exchange step. After dialysis to remove the salt, the pooled active fractions were purified to apparent homogeneity on a MonoQ column eluted with sequential linear gradients consisting first of a 2%/min gradient to buffer containing 0.3 M NaCl followed by a steep gradient 0.5 M NaCl. The enzyme eluted as a sharp, symmetrical, well-isolated peak at approximately 0.4 M NaCl. DKGRd was not as over-expressed bound less tightly to the Matrix Red Agarose and MonoQ resins. DKGRd was eluted from the Matrix Red Agarose column with a 100 ml linear gradient of 0-1.5 M NaCl. Gel electrophoresis analysis revealed that several cellular proteins coeluted with the reductase at this salt concentration. Fractionation of this material on the MonoQ column, failed to separate the reductase from one of the major cellular contaminants. A second MonoQ column was performed at pH 8.0 using a shallow gradient of salt concentration through the region where the reductase eluted. The resulting protein was free of major contaminants and was estimated by densitometry to be greater than 97 percent pure. Purified DKGRc and DKGRd had apparent native molecular weights 30 and 31 kD, respectively. The observed molecular weights corresponded roughly to those predicted by the gene sequences of 29,687 and 33,798 daltons, respectively.

Example 3

Characterization of Environmental Reductases

Materials and Methods:

The product of the reduction of 2,5-DKG by the purified enzymes was determined by gas chromatography/mass spectrometry (GCMS). First, a high concentration preparation of 2,5-diketo-D-gluconic acid was prepared from permeabilized cells. Cells were grown and permeabilized as described above. The treated cells (50 ml in a 250 ml notched flask) were incubated with 50 mM glucose for 6 hours at 28° C. and 250 rpm. Cells were then removed by centrifugation and supernatant was passed through a 0.22 micron filter to remove all viable cells. The concentration of 2,5, DKG was determined enzymatically to be 32 mM. For conversion to product, the preparation was diluted to give a solution of 1 ml that contained 10 µmol substrate in 65 mM Bis/Tris buffer at pH 7.0. Five µmol NADPH was added, and the reaction was initiated by addition of 40 Units of purified DKGRc or 52 Units of purified DKGRd. The progress of the reactions was monitored by determining the concentration of NADPH remaining; 10 µl samples of the reaction were diluted into 0.99 ml Tris buffer and absorbance at 340 nm was measured. Once the undiluted reaction mixture reached an $OD_{340}$ of less than 2.0, an additional 5 µmol of NADPH was added to give a total of 10 µmol. An additional aliquot of purified enzyme was also added. The conversion was verified by HPLC. Once conversion of NADPH was complete the samples were analyzed by HPLC and stored at −80° C.

Standard enzymatic assays for the reduction of 2,5-diketo-D-gluconic acid were preformed at 30° C. in 1.0 ml of 100 mM Tris/HCl buffer, pH 7.2, containing 0.1 mM NADPH and 1 mM 2,5-diketo-D-gluconic acid. The decrease in absorbance due to the oxidation of NADPH was measured using a Shimadzu UV 160U spectrophotometer. One unit of enzyme is defined as the amount of enzyme that catalyzed the oxidation of 1 µmol of NADPH per minute. For determination of the pH optima, solutions of a 100 mM Bis-Tris and Bis-Tris propane were prepared in 0.5 pH unit increments from pH 5.5 to 9.0. The enzymes were assayed at each pH level to determine optimal activity.

Kinetic parameters of the environmental 2,5-diketo-D-gluconic acid reductases (DKGRc and DKGRd) were evaluated in duplicate, and were calculated by a least squares fit of the data to the hyperbola using the curvefitting algorithm of DeltaGraph (DeltaPoint, Monterey, Calif.) or Prism (GraphPad Software, San Diego, Calif.). Cosubstrates were present at the concentrations described for the standard assay (described above). For determination of the Km for NADPH and NADH, assays were performed using a Varian Cary 1G spectrophotometer.

For determination of the parameters for NADH-dependent activity (present only in DKGRc), higher concentrations of both cofactor and substrate were required. Consequently, the initial absorbance at 340 nm was above the linear range of the spectophotometer, and the change in absorbance was measured at 385 nm. Because the extinction coefficient of NADH at 385 nm was 7.74 fold lower than at 340 nm, the rate data were adjusted accordingly.

For determination of the pH optima of the enzymes, solutions of a 100 mM Bis/Tris and Bis/Tris propane were prepared in 0.5 pH unit increments from pH 5.5 to 9.0. The enzymes were assayed at each pH level to determine optimal activity.

Protein concentrations were assayed by the method of Bradford using the protocol and reagent from Bio-Rad Laboratories with bovine serum albumin as a standard.

The thermal stability of each reductase was evaluated at low protein concentrations (0.085 mg/ml) in 100 mM Bis/Tris buffer, pH 7.0. The half-life at 45° C. was determined by incubating 30 µl aliquots of purified enzyme in thin-walled PCR tubes at 4° C. The temperature was shifted rapidly to 45° C. by means of a Robocycler Gradient 96 thermal cycler (Stratagene, Inc.), and held at 45° C. for 0.5, 5, 10, 20, 30, or 60 minutes before returning the sample to 4° C. Each tube was assayed later by the standard procedure. The midpoint temperature of thermal inactivation of DKGRd was determined by incubating the enzyme for 10 min over a range of temperatures defined by the Robocycler. The Robocycler was programmed to move samples from 4° C. to a gradient of defined temperatures ranging from 30-52° C. in 2° C. increments. After 10 min the samples were returned to 4° C. The stability of DKGRc at 30° C. was determined by placing aliquots of the enzyme in prewarmed microfuge tubes in a 30° C. waterbath. The tubes were incubated for 1 through 5 hours, removed and assayed. The rate constants for loss of activity was determined by fit to the equation for exponential decay using Prism (GraphPad, Inc.). All samples were assayed in duplicate.

Results:

Previously, reduction of 2,5-diketo-D-gluconic acid by extracts containing the overexpressed environmental reductases was stoichiometric and gave a product that comigrated with 2-keto-L-gulonic acid on HPLC. However, complications could arise in extracts, and standards are not available for all four of the possible products formed by reduction of 2,5-diketo-D-gluconic acid. Therefore, a concentrated solution of 2,5-diketo-D-gluconic acid was prepared and converted to product by each reductase as described above. The concentration of 2,5-diketo-D-gluconic acid in the reaction mixture was 10 mM. Following addition of purified enzyme (40-52 Units) and a slight excess of NADPH relative to 2,5-diketo-D-gluconic acid, HPLC analysis revealed that all the 2,5-diketo-D-gluconic acid had been converted to a compound that coeluted with authentic 2-keto-L-gulonic acid. The reaction mixture was subsequently analyzed by GCMS. The product of both reactions had a mass spectrum identical to that of authentic 2-keto-L-gulonic acid (FIG. 5). All other components present in the chromatogram were identified as derivatives of buffer components or derivitization reagents (data not shown). No other product derived from 2,5-diketo-D-gluconic acid was observed.

Kinetic parameters of the environmental 2,5-diketo-D-gluconic acid reductases were determined at 30° C. (Table 3). The $K_m$ values determined for 2,5-diketo-D-gluconic acid were 57 and 67 µM for forms c and d, respectively. These values are much lower than those reported for the *Corynebacterium* reductases (Sonoyama, T. and K. Kobayashi, *J. Ferment. Technol.* 65:311-317 (1987)). The observed $k_{cat}$ for both environmental forms was closer to that of the more active *Corynebacterium* enzyme (Table 3). As a result, the calculated $k_{cat}/K_m$ values were much higher for the environmental forms. The new 2,5-diketo-D-gluconic acid reductases had catalytic efficiencies more than 20 times higher than the *Corynebacterium* form a enzyme, and 1000 times higher than the form b enzyme.

TABLE 3

Kinetic parameters of purified 2,5-diketo-D-gluconic acid reductases.

| Form | $K_m$, DKG (µM) | $k_{cat}$ (s$^{-1}$) | $k_{cat}/K_m$ (mM$^{-1}$s$^{-1}$) | $K_m$, NA (µM) |
|---|---|---|---|---|
| a | 13,500 | 4 | 0.3 | 13 |
| b | 2,000 | 39 | 19 | 10 |
| c | 57 | 31 | 550 | 3.0 |
| d | 67 | 27 | 400 | 2.7 |

The pH profiles of both reductases revealed a preference for acidic pH, but good activity was observed at all pH values below 7.5 (FIG. 6). Both enzymes demonstrate optimum activity at pH 6.0. This trend was observed for all buffers evaluated, but activity varied dependent on the buffer used. Amine buffers such as Tris and Bis-Tris gave the best activity. In phosphate and pyrophosphate buffers both enzymes were approximately one-third as active at pH 6.0. Sulfonate buffers such as MES and HEPES gave intermediate activities. The preference of the DKGRd for acidic pH was slightly more pronounced.

With a few exception, aldo-keto reductases are absolutely specific for NADPH as cosubstrate, including the *Corynebacterium* 2,5-diketo-D-gluconic acid reductases (Ratnam, et al., *Biochemistry* 38(24):7856-64 (1999); Todaka, et al., *Superfamily Arch Biochem Biophys.* 374 (2) 189-197 (2000)). When extracts of induced cells were fractionated by non-denaturing polyacrylamide gel electrophoresis and incubated with NADH or NADPH, bands of 2,5-diketo-D-gluconic acid-dependent oxidation of both cofactors was observed (data not shown). These bands, which were absent in uninduced cells, were located at the same position in the gel suggesting that one enzyme catalyzed both reactions. Analyses of the purified enzymes confirmed that they were responsible for the observed reaction (FIG. 7A). However, catalysis was less efficient with NADH as cosubstrate (Table 4). The $K_m$ value for NADH was nearly three orders of magnitude higher than for NADPH. The apparent $k_{cat}$ and $k_{cat}/K_m$ values were also much lower than those measured with NADPH as cosubstrate. Substitution of NADH for NADPH also effected the apparent $K_m$ for 2,5-diketo-D-gluconic acid dramatically, increasing it 17 to 40 fold (Tables 4 and 5). The NADH-dependent activity was enhanced by inclusion of inorganic phosphate in the reaction buffer (FIG. 7B). The stimulation was saturable, with an apparent $K_m$ of 1.3 mM, indicating that the phenomenon was due to binding of inorganic phosphate to the enzyme.

TABLE 4

Comparison of kinetic parameters with NADH as cofactor.

| Form | $K_{m, nadh}$ (µM) | $k_{cat}$ (s$^{-1}$) | $k_{cat}/K_{m, nadh}$ (mM$^{-1}$s$^{-1}$) | $K_{m, dkg}$ (µM) | $K_{m, Pi}$ (mM) |
|---|---|---|---|---|---|
| c | 1800 | 1.6 | 0.9 | 2,260 | 16.8 |
| d | 3900 | 12.2 | 3.1 | 1,150 | 10.6 |

*Corynebacterium* reductases are somewhat labile thermally (Powers, D. B. and S. Anderson, U.S. Pat. No. 5,795,761 (1998); Sonoyama, T. and K. Kobayashi, *J. Ferment. Technol.* 65:311-317 (1987)). To establish the thermal stability of the environmental reductases, each environmental reductase was incubated at 44° C. for various periods of time. A robotic PCR thermal cycler (Robocycler Gradient 96, Stratagene, Inc.) was used establish temperatures rapidly and precisely. Under these conditions, DKGRc was quite labile, losing over half its activity at the earliest time point, 0.5 min. Its half-life was estimated to be 0.4 min. In contrast, DKGRd was relatively stable under these conditions, with a half-life of 53.4 min. The thermal inactivation temperature of DKGRd was determined by incubating the enzyme for 10 min over a temperature gradient established by the Robocycler (FIG. 8). The enzyme retained nearly complete activity up to 45° C., after which the activity declined rapidly. The temperature under which half the activity was lost under these conditions was estimated to be 47° C.

Example 4

Construction of Site Specific Mutants of Environmental Reductase DKGRc

Materials and Methods:

Site specific mutants of DKGRc were constructed by overlap extension PCR. Oligonucleotides were designed to convert two positively charged residues implicated in the binding of the adenosine-2'-phosphate of NADPH, K232 and R238, to neutral residues. The oligonucleotides:

```
5-ATCAGGGTTCGAAGACTGTGG      (SEQ ID NO: 42)

5-TCTTCGAACCCTGATCAACTTG     (SEQ ID NO: 43)
``` were complementary to the antisense and sense strands, respectively, and introduced the changes K232Q and R238Q, respectively. The bases that differ from the native sequence are underlined. Each oligonucleotide was paired with the appropriate adapter primer (i.e. primers for amplifying the gene for insertion into expression vectors) in PCR's to generate fragments of the DKGRc gene that incorporated one of the two changes. Primers were also synthesized that matched the native DNA sequence. When used with the appropriate adapter primer, these generated an unmodified fragment of the gene. The gene fragments were combined pairwise in overlap extension PCR reactions to give the K232Q and the R238Q mutants. The amplification of the full-length genes was driven by addition of both adapter primers. The R238Q mutant was purified by the procedure used for purification of native DGKRc, but eluted at a different position in the salt gradients, as expected.

Results:

Extracts prepared from induced samples of the K232Q and R238Q mutants showed comparable, strong overexpression of the reductase protein based on gel electrophoresis, but the NADPH-dependent activity was much reduced. Modest activity was detected in extracts of the R238Q mutant, but very low activity was observed for the K232Q mutant. The R238Q mutant was purified to homogeneity and analyzed kinetically (Table 5). The $K_m$ for NADPH was 18-fold higher in mutant reductase, as anticipated for removal of a residue implicated in charge-charge interaction with the adenosine-2'-phosphate. However, the maximum activity of the enzyme increased in the presence of the mutation, indicated by 3.5-fold increase in $k_{cat}$. The overall catalytic efficiency (with respect to the $K_m$ of NADPH) was one-fifth that of the native enzyme.

The $K_m$ for NADH, in contrast, was not affected by the mutation (Table 5), but a similar increase in $k_{cat}$ was observed with NADH as cosubstrate. As a result, the catalytic efficiency with NADH as cosubstrate increased 7-fold due to the mutation. Nonetheless, due to the far higher $K_m$ for NADH, the efficiency of the mutant enzyme remained much higher with NADPH as cosubstrate even after the mutation. Replacement of the arginine with glutamine also affected the enzyme's interaction with the substrate, 2,5-diketo-D-gluconic acid; its $K_m$ increased 7.7-fold from 57 to 440 µM.

TABLE 5

Kinetic parameters of DKGRc and its R238Q mutant.

| Form | $K_{m, nadph}$ (mM) | $k_{cat}$ ($S^{-1}$) | $k_{cat}/K_{m, nadph}$ ($mM^{-1}s^{-1}$) | $K_{m, nadh}$ (mM) | $k_{cat}$ ($S^{-1}$) | $k_{cat}/K_{m, nadh}$ ($mM^{-1}s^{-1}$) |
|---|---|---|---|---|---|---|
| native | 0.003 | 31 | 10,300 | 1.8 | 1.6 | 0.9 |
| R238Q | 0.055 | 108 | 1,960 | 1.9 | 12 | 6.3 |

We claim:

1. A process for converting glucose to ascorbic acid comprising culturing a host cell comprising a nucleotide sequence which encodes a peptide having an amino acid sequence which has at least about 95% sequence identity to an amino acid sequence of SEQ ID NO:8, wherein said conversion of glucose to ascorbic acid is conducted under conditions suitable for the expression of 2,5-diketo-D-gluconic acid reductase.

* * * * *

SEQUENCE LISTING

<160> NUMBER OF SEQ ID NOS: 43

<210> SEQ ID NO 1
<211> LENGTH: 380
<212> TYPE: DNA
<213> ORGANISM: Artificial Sequence
<220> FEATURE:
<223> OTHER INFORMATION: pI-14 clone

<400> SEQUENCE: 1

```
ggctaccggc agatcgacac ggcagcaatc tatgacaatg aggcagaggt cggagctgcg      60
gttcgcaaaa gtggcctcgc gcgcgaggaa gtttttgtga catcaaagat ttggaacgac     120
agacacggat accacgaggc gaaagaagcc attcaagagt cgattgatcg actcaacatc     180
gactatgtcg acatgatgct gattcactgg ccgtgcccga agcaagacaa gtttgttgag     240
acttggcacg cattcgaaga ggtgctcgaa actggcttgg ttaagggcat cggagtctcg     300
aactttaatc aaccccatct cgagaagctc ttgcagcact caaacatcac gccggcaatt     360
aaccaggtcg agctgcaccc                                                 380
```

<210> SEQ ID NO 2
<211> LENGTH: 380
<212> TYPE: DNA
<213> ORGANISM: Artificial Sequence
<220> FEATURE:
<223> OTHER INFORMATION: pI-28 clone

<400> SEQUENCE: 2

```
ggctaccggc agatcgacac cgctgcactt tatgacaacg aggccgaggt tggagctgcc      60
attcgcaaga gcggtctaga ccgcgaagag attttcgtaa cctcaaagat ttggaatgac     120
cgccacggat accacgaggc aaaagatgcc attcaagagt cggtcgacag actcaacatc     180
ggctatgtcg acatgatgct tattcactgg ccgtgcccaa agcaagacaa gttcgtcgaa     240
acctggcacg ctttcgaaga agtgctcgaa accggattgg tgaaatcaat cggtgtctca     300
aactttcacc aacaccacct agaaaaactt cttgcggctg cgaatgttgt gccggcgatc     360
aaccagatcg agctccaccc                                                 380
```

<210> SEQ ID NO 3
<211> LENGTH: 371
<212> TYPE: DNA
<213> ORGANISM: Artificial Sequence

```
<220> FEATURE:
<223> OTHER INFORMATION: pII-04 clone

<400> SEQUENCE: 3
ggctaccggc tgatcgacac cgcggccgct tataagaatg aggaggctgt tggcaaagcg      60
atcaaaggaa gcggcgtcgc aagggaagaa gttttcgtca ctaccaagct ctgggtttcg     120
gacgcgggtt acgaaagtgc gaagaaggct ttcgataggt cactgaagcg cttgcaactg     180
gattacttgg atctgtatct gatccatcaa ccttacgggg acgtctacgg ttcatggagg     240
gcgatggaag aactgttgcg tgagggcagg atcagagcga taggcgtcag caacttccaa     300
ccagaccggt tgatggatct gatggttcac aaccaggtag ttccagcagt caaccaggtc     360
gagctgcacc c                                                          371

<210> SEQ ID NO 4
<211> LENGTH: 377
<212> TYPE: DNA
<213> ORGANISM: Artificial Sequence
<220> FEATURE:
<223> OTHER INFORMATION: pIII-06 clone

<400> SEQUENCE: 4
ggctaccgac agatcgacac cgcggcgttt tacggcaacg agacggaaaa tggcgaaggc      60
ctgcgccagt cggggatcaa gcgcgaggag gtcttcatct gcaccaaggt caggcagggc     120
gatctgatgc ccgatgcctt tgcccaggtg cttgagcaga gcctcgccaa cctcaagctt     180
ccttacgttg atcttctgct gatccactgg aacaaccctg acgttccctt caagttgtcc     240
gtcggcgcgc tctgcaaggc caagaaggaa ggcaagacca agcacatcgg tgtcgccaat     300
ttcaccacga ccatgctgga tgaggcttgg gccgtgacgt cggagccact cgtctgcaac     360
caggtcgagc tgcaccc                                                    377

<210> SEQ ID NO 5
<211> LENGTH: 410
<212> TYPE: DNA
<213> ORGANISM: Artificial Sequence
<220> FEATURE:
<223> OTHER INFORMATION: pIII-19 clone

<400> SEQUENCE: 5
ggctaccggc agatcgacac cgcagagggc taccaaaatg aatcgggcgt cggggtggga      60
attcggaagg cgctcgagtc cgagggtctc gcgcgaagcg ctctcttcgt caccacgaag     120
ctctggcccg ggaacccagt gtgggggcag ccggcgaaga ccaccgactc cacggtgaca     180
tcgctcgacg agagtctcga acggctgggg ctagactacg tcgaccttta tttgatccat     240
gcaccgtacg aacgaaacca gagactcgcc cagtggcgtg ggctcctcga gccgaagcgg     300
cagggaaagg cgcgggcgat cggcgtgagc aactttagca tcaggcacat cgaggagcta     360
acggcagcgg gcctgcccat gccagctgcc aaccagatcg agctccaccc                410

<210> SEQ ID NO 6
<211> LENGTH: 371
<212> TYPE: DNA
<213> ORGANISM: Artificial Sequence
<220> FEATURE:
<223> OTHER INFORMATION: pIII-24 clone

<400> SEQUENCE: 6
ggctaccggc agatcgacac agctgcctcg tatggaaatg aaaaggaagt tggacgggca      60
atagccacga gtggcatccc tcgtggggac cttttcatca cgacaaagca ctggatacaa     120
```

```
tccggtggag agagtagtac gaagaaagca ttcgaacaat cactcaagcg gcttgggcta    180
gactatattg atctctatct catccatcaa ccctcgggg actactatag tgaatggcga    240
gcaatggaag agctatataa acaggggcgc gcaaaagcta tcggtgtttc aaacttttc    300 cccgatcgac tcgttgatct catcgaacac aacacagtag cgccagcagt caaccagatc    360
gagctccacc c                                                         371
```

<210> SEQ ID NO 7
<211> LENGTH: 1413
<212> TYPE: DNA
<213> ORGANISM: Artificial Sequence
<220> FEATURE:
<223> OTHER INFORMATION: pI-14 full length clone

<400> SEQUENCE: 7

```
cgaatgcgtg ccaagtctca aggagtagtc atggccgttt tcgctgtcac ctatctatac     60
agcgctgagc ctgacgattt gaacctcgtg cgcccargtc accgagcttg gctagccgac    120
cgcctagaag acggttctct gctcrccagc ggcccaatgg ycgataaccc aaccgcactg    180
ctgatttggy gagccgaatc gctcgaagcg ttggctaagt tgctagatca agacccttc    240 gacatcgcgg gctacatcgg cgagcgaacg atcaccgagt ggaaccccgt ttttggccct    300
tggagcgctc agtgagcgca gaacagcctc gcctgattct caactctggg caatcgatgc    360
cgcagcttgg tctcggcgca tacaaggtga atcaagacat cgcggygcaa ctggtgcagc    420
acgcactcga atcggctac cgacgaatcg acacggcagc actctatgac aatgaggcag    480
aggtcggagc tgcggttcgc aaaagtggcc tcgcgcgcga ggaagttttt gtgacatcaa    540
agatttggaa cgacagacac ggataccacg aggcgaaaga agccattcaa gagtcgattg    600
atcgactcaa catcgactat gtcgacatga tgctgattca ctggccgtgc ccgaagcaag    660
acaagtttgt tgagacttgg cacgcattcg aagaggtgct cgaaactggc ttggttaagg    720
gcatcggagt ctcgaacttt aatcaacccc atctcgagaa gctcttgcag cactcaaaca    780
tcacgccggc aattaaccag gttgagttgc acccacaact agctcaaaat gggcttcgtg    840
aattcaatga aagacatggc attcgcactg aggcttgggc cccacttggc cgtgcccgtt    900
ycatgcagca ccccctgtta gttgagattg ccractcact kggcaagagc gttgcgcagg    960
tcataattcg ctggcacctg caaattggca atcttgtaat tccraagtct tcgaacccag   1020
rtcgacttgc craaaacttc gacgtcttcg atttcgaact gagccaccac aacatgagca   1080
tcattgcaac tctcaacact gaaacacgaa ttgccaccaa tcctgacgat atgaattaga   1140
ggaaacatgc gcgttctagt arctggagca accggactca tcggcaccga agtaattcga   1200
caactcaagg ctcgtggcga cgaggttgtc actatggttc gtcgcacacc cactagcgaa   1260
acacagcgtg agtggcagcc agaccgcggt taccttcagc cgggyacgct cgatggcatc   1320
gacgctgtcg taaacctcgc tggggcgaca accggcaaac tcccctggac gaagaaatac   1380
aagcatgagc tcatctggtc tcgagccgcc cct                                1413
```

<210> SEQ ID NO 8
<211> LENGTH: 275
<212> TYPE: PRT
<213> ORGANISM: Artificial Sequence
<220> FEATURE:
<223> OTHER INFORMATION: pI-14 clone

<400> SEQUENCE: 8

Met Ser Ala Glu Gln Pro Arg Leu Ile Leu Asn Ser Gly Gln Ser Met

```
                1               5                  10                  15
Pro Gln Leu Gly Leu Gly Ala Tyr Lys Val Asn Gln Asp Ile Thr Val
            20                  25                  30

Gln Leu Val Gln His Ala Leu Glu Ile Gly Tyr Arg Arg Ile Asp Thr
            35                  40                  45

Ala Ala Ile Tyr Asp Asn Glu Ala Glu Val Gly Ala Ala Val Arg Lys
            50                  55                  60

Ser Gly Leu Ala Arg Glu Glu Val Phe Val Thr Ser Lys Ile Trp Asn
65                  70                  75                  80

Asp Arg His Gly Tyr His Glu Ala Lys Glu Ala Ile Gln Ser Ile
                    85                  90                  95

Asp Arg Leu Asn Ile Asp Tyr Val Asp Met Met Leu Ile His Trp Pro
                100                 105                 110

Cys Pro Lys Gln Asp Lys Phe Val Glu Thr Trp His Ala Phe Glu Glu
                115                 120                 125

Val Leu Glu Thr Gly Leu Val Lys Gly Ile Gly Val Ser Asn Phe Asn
            130                 135                 140

Gln Pro His Leu Glu Lys Leu Leu Gln His Ser Asn Ile Thr Pro Ala
145                 150                 155                 160

Ile Asn Gln Val Glu Leu His Pro Gln Leu Ala Gln Asn Gly Leu Arg
                165                 170                 175

Glu Leu Asn Glu Arg His Gly Ile Arg Thr Glu Ala Trp Ala Pro Leu
                180                 185                 190

Gly Arg Ala Arg Phe Met Gln His Pro Leu Leu Ile Glu Ile Ala Glu
                195                 200                 205

Ser Leu Gly Lys Ser Val Ala Gln Val Ile Ile Arg Trp His Leu Gln
            210                 215                 220

Ile Gly Asn Leu Val Ile Pro Lys Ser Ser Asn Pro Asp Arg Leu Ala
225                 230                 235                 240

Glu Asn Phe Asp Val Phe Asp Phe Glu Leu Ser His His Asn Met Ser
                245                 250                 255

Ile Ile Ala Thr Leu Asn Thr Glu Thr Arg Ile Ala Thr Asn Pro Asp
                260                 265                 270

Asp Met Asn
        275

<210> SEQ ID NO 9
<211> LENGTH: 1183
<212> TYPE: DNA
<213> ORGANISM: Artificial Sequence
<220> FEATURE:
<223> OTHER INFORMATION: pI-28 full length clone

<400> SEQUENCE: 9
tsgaccaaga cccattcgaa catcgctggc taacatcggc gagcgcacaa tcaccgagtg      60
gaaccccgta ttcggcccgt ggagccaaaa ctaatggcat cgccgctggt tacactcaac     120
gacggccgcc taatgccgca gctcggactg ggcgtataca aggtcaatca agacatcgcc     180
gttcagctcg tgcagaccgc aatcgagatt ggctatcgcc gcgtcgacac cgctgctctt     240
tatgacaacg aggccgaggt tggmgctgcc attcgcaaga gyggkctmga ccgcgaagag     300
attttcgtaa cctcaaagat ttggaatgac cgccacggat accacgaggc aaaagatgcc     360
attcaagagt cggtcgacag actcaacatc ggctatgtcg acatgatgct tattcactgg     420
ccgtgcccaa agcaagacaa gttcgtcgaa acctggcacg ctttcgaaga agtgctcgaa     480
accggattgg tgaaatcaat cggtgtctca aactttcacc aacaccacct agaaaaactt     540
```

```
cttgcggctg cgaatgttgt gccggcgatc aaccaggtcg agctgcaccc acagctcgca    600
cagaattcgc tgcgccactt caacaagcag cacaacatca aractgaggc ctgggctccc    660
ctgggtcgcg cmaagtttyt agagaacccg ctgcttgtcg aaattgcaga atcgcttggc    720
aagagcgttg ctcaggtaat aattcgctgg cacctgcart tgcagaatct tgttattccg    780
aaatcttcaa acccagatcg tctcgcagag aacttcgacg ttttcgactt tgaacttagc    840
cagcaccaaa tgggcataat cgcaacactg aacacagaaa ctcgaatcgc caccaaccca    900
gacgacatga attagagaag aaaatgcgcg ttcttgtaac cggagcaacc ggactaatcg    960
gcaccgaagt aattcgccar mtaaaggctc gaggcgacga ggtcgtcaca atggtgcgca    1020
gagcgccgca gaacgattca gagcgcgart ggcagccaga tcgcggttac cttcagccag    1080
acacgcttga cggcattgac gcggtggtra acctygcggg tgcaaccacc ggaaaacttc    1140
cgtggacaaa gaaatacaag gatgagctca tctggtctcg agc                     1183
```

<210> SEQ ID NO 10
<211> LENGTH: 273
<212> TYPE: PRT
<213> ORGANISM: Artificial Sequence
<220> FEATURE:
<223> OTHER INFORMATION: pI-28 clone

<400> SEQUENCE: 10

```
Met Ala Ser Pro Leu Val Thr Leu Asn Asp Gly Arg Leu Met Pro Gln
  1               5                  10                  15

Leu Gly Leu Gly Val Tyr Lys Val Asn Gln Asp Ile Ala Val Gln Leu
             20                  25                  30

Val Gln Thr Ala Ile Glu Ile Gly Tyr Arg Arg Val Asp Thr Ala Ala
         35                  40                  45

Leu Tyr Asp Asn Glu Ala Glu Val Gly Ala Ala Ile Arg Lys Ser Gly
     50                  55                  60

Leu Glu Arg Glu Glu Ile Phe Val Thr Ser Lys Ile Trp Asn Asp Arg
 65                  70                  75                  80

His Gly Tyr His Glu Ala Lys Glu Ala Ile Gln Glu Ser Val Asp Arg
                 85                  90                  95

Leu Asn Ile Gly Tyr Val Asp Met Met Leu Ile His Trp Pro Cys Pro
            100                 105                 110

Lys Gln Asp Lys Phe Val Glu Thr Trp His Ala Phe Glu Glu Val Leu
        115                 120                 125

Glu Thr Gly Leu Val Lys Ser Ile Gly Val Ser Asn Phe His Gln His
    130                 135                 140

His Leu Glu Lys Leu Leu Ala Ala Ala Thr Val Val Pro Ala Ile Asn
145                 150                 155                 160

Gln Val Glu Leu His Pro Gln Leu Ala Gln Asn Ser Leu Arg His Phe
                165                 170                 175

Asn Lys Gln His Asn Ile Lys Thr Glu Ala Trp Ala Pro Leu Gly Arg
            180                 185                 190

Ala Lys Phe Leu Glu Asn Pro Leu Leu Val Glu Ile Ala Glu Ser Leu
        195                 200                 205

Gly Lys Ser Val Ala Gln Val Ile Ile Arg Trp His Leu Gln Leu Gln
    210                 215                 220

Asn Leu Val Ile Pro Lys Ser Ser Asn Pro Asp Arg Leu Ala Glu Asn
225                 230                 235                 240

Phe Asp Val Phe Asp Phe Glu Leu Ser Gln His Gln Met Gly Ile Ile
                245                 250                 255
```

Ala Thr Leu Asn Thr Glu Thr Arg Ile Ala Thr Asn Pro Asp Asp Met
            260                 265                 270

Asn

<210> SEQ ID NO 11
<211> LENGTH: 20
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (1)...(20)
<223> OTHER INFORMATION: n = A,T,C or G

<400> SEQUENCE: 11
ggctaccgnc wsmtcgacac                                                   20

<210> SEQ ID NO 12
<211> LENGTH: 20
<212> TYPE: DNA
<213> ORGANISM: Artificial Sequence
<220> FEATURE:
<223> OTHER INFORMATION: primer

<400> SEQUENCE: 12
gggtgsagct cgayctggtt                                                   20

<210> SEQ ID NO 13
<211> LENGTH: 22
<212> TYPE: DNA
<213> ORGANISM: Artificial Sequence
<220> FEATURE:
<223> OTHER INFORMATION: primer

<400> SEQUENCE: 13
ctatgacaat gaggcagagg tc                                                22

<210> SEQ ID NO 14
<211> LENGTH: 25
<212> TYPE: DNA
<213> ORGANISM: Artificial Sequence
<220> FEATURE:
<223> OTHER INFORMATION: primer

<400> SEQUENCE: 14
cgcgcgcgag gaagtttttg tgaca                                             25

<210> SEQ ID NO 15
<211> LENGTH: 20
<212> TYPE: DNA
<213> ORGANISM: Artificial Sequence
<220> FEATURE:
<223> OTHER INFORMATION: primer

<400> SEQUENCE: 15
ccgtgcccga agcaagacaa                                                   20

<210> SEQ ID NO 16
<211> LENGTH: 22
<212> TYPE: DNA
<213> ORGANISM: Artificial Sequence
<220> FEATURE:
<223> OTHER INFORMATION: primer

<400> SEQUENCE: 16

```
accccatctc gagaagctct tg                                          22

<210> SEQ ID NO 17
<211> LENGTH: 20
<212> TYPE: DNA
<213> ORGANISM: Artificial Sequence
<220> FEATURE:
<223> OTHER INFORMATION: primer

<400> SEQUENCE: 17
tcataattcg ctggcacctg                                             20

<210> SEQ ID NO 18
<211> LENGTH: 20
<212> TYPE: DNA
<213> ORGANISM: Artificial Sequence
<220> FEATURE:
<223> OTHER INFORMATION: primer

<400> SEQUENCE: 18
gccgttttcg ctgtcaccta                                             20

<210> SEQ ID NO 19
<211> LENGTH: 22
<212> TYPE: DNA
<213> ORGANISM: Artificial Sequence
<220> FEATURE:
<223> OTHER INFORMATION: primer

<400> SEQUENCE: 19
gctgcaagag cttctcgaga tg                                          22

<210> SEQ ID NO 20
<211> LENGTH: 25
<212> TYPE: DNA
<213> ORGANISM: Artificial Sequence
<220> FEATURE:
<223> OTHER INFORMATION: primer

<400> SEQUENCE: 20
agttcgagac tccgatgccc ttaac                                       25

<210> SEQ ID NO 21
<211> LENGTH: 21
<212> TYPE: DNA
<213> ORGANISM: Artificial Sequence
<220> FEATURE:
<223> OTHER INFORMATION: primer

<400> SEQUENCE: 21
cgaatgcgtg ccaagtctca a                                           21

<210> SEQ ID NO 22
<211> LENGTH: 22
<212> TYPE: DNA
<213> ORGANISM: Artificial Sequence
<220> FEATURE:
<223> OTHER INFORMATION: primer

<400> SEQUENCE: 22
gacctctgcc tcattgtcat ag                                          22

<210> SEQ ID NO 23
<211> LENGTH: 20
<212> TYPE: DNA
<213> ORGANISM: Artificial Sequence
<220> FEATURE:
```

<223> OTHER INFORMATION: primer

<400> SEQUENCE: 23
cgccacgagc cttgagttgt                                               20

<210> SEQ ID NO 24
<211> LENGTH: 22
<212> TYPE: DNA
<213> ORGANISM: Artificial Sequence
<220> FEATURE:
<223> OTHER INFORMATION: primer

<400> SEQUENCE: 24
tttcttcgtc caggggagtt tg                                            22

<210> SEQ ID NO 25
<211> LENGTH: 20
<212> TYPE: DNA
<213> ORGANISM: Artificial Sequence
<220> FEATURE:
<223> OTHER INFORMATION: primer

<400> SEQUENCE: 25
gcgtgcccgg ctgaaggtaa                                               20

<210> SEQ ID NO 26
<211> LENGTH: 30
<212> TYPE: DNA
<213> ORGANISM: Artificial Sequence
<220> FEATURE:
<223> OTHER INFORMATION: primer

<400> SEQUENCE: 26
gagaacaatt gtatgagcgc agaacagcct                                    30

<210> SEQ ID NO 27
<211> LENGTH: 35
<212> TYPE: DNA
<213> ORGANISM: Artificial Sequence
<220> FEATURE:
<223> OTHER INFORMATION: primer

<400> SEQUENCE: 27
tcttctaagc ttcactaatt catatcgtca ggatt                              35

<210> SEQ ID NO 28
<211> LENGTH: 22
<212> TYPE: DNA
<213> ORGANISM: Artificial Sequence
<220> FEATURE:
<223> OTHER INFORMATION: primer

<400> SEQUENCE: 28
ttatgacaac gaggccgagg tt                                            22

<210> SEQ ID NO 29
<211> LENGTH: 22
<212> TYPE: DNA
<213> ORGANISM: Artificial Sequence
<220> FEATURE:
<223> OTHER INFORMATION: primer

<400> SEQUENCE: 29
gccattcaag agtcggtcga ca                                            22

<210> SEQ ID NO 30

```
<211> LENGTH: 22
<212> TYPE: DNA
<213> ORGANISM: Artificial Sequence
<220> FEATURE:
<223> OTHER INFORMATION: primer

<400> SEQUENCE: 30
cgaaaccgga ttggtgaaat ca                                              22

<210> SEQ ID NO 31
<211> LENGTH: 22
<212> TYPE: DNA
<213> ORGANISM: Artificial Sequence
<220> FEATURE:
<223> OTHER INFORMATION: primer

<400> SEQUENCE: 31
ttcttgcggc tgcgaatgtt gt                                              22

<210> SEQ ID NO 32
<211> LENGTH: 20
<212> TYPE: DNA
<213> ORGANISM: Artificial Sequence
<220> FEATURE:
<223> OTHER INFORMATION: primer

<400> SEQUENCE: 32
tcggcccgtg gagccaaaac                                                 20

<210> SEQ ID NO 33
<211> LENGTH: 22
<212> TYPE: DNA
<213> ORGANISM: Artificial Sequence
<220> FEATURE:
<223> OTHER INFORMATION: primer

<400> SEQUENCE: 33
acaacattcg cagccgcaag aa                                              22

<210> SEQ ID NO 34
<211> LENGTH: 23
<212> TYPE: DNA
<213> ORGANISM: Artificial Sequence
<220> FEATURE:
<223> OTHER INFORMATION: primer

<400> SEQUENCE: 34
gaaagtttga gacaccgatt gat                                             23

<210> SEQ ID NO 35
<211> LENGTH: 22
<212> TYPE: DNA
<213> ORGANISM: Artificial Sequence
<220> FEATURE:
<223> OTHER INFORMATION: primer

<400> SEQUENCE: 35
accgattgat ttcaccaatc cg                                              22

<210> SEQ ID NO 36
<211> LENGTH: 22
<212> TYPE: DNA
<213> ORGANISM: Artificial Sequence
<220> FEATURE:
<223> OTHER INFORMATION: primer

<400> SEQUENCE: 36
```
ttgcctcgtg gtatccgtgg cg                                                22

<210> SEQ ID NO 37
<211> LENGTH: 22
<212> TYPE: DNA
<213> ORGANISM: Artificial Sequence
<220> FEATURE:
<223> OTHER INFORMATION: primer

<400> SEQUENCE: 37
tacgaaaatc tcttcgcggt ct                                                22

<210> SEQ ID NO 38
<211> LENGTH: 22
<212> TYPE: DNA
<213> ORGANISM: Artificial Sequence
<220> FEATURE:
<223> OTHER INFORMATION: primer

<400> SEQUENCE: 38
aacctcggcc tcgttgtcat aa                                                22

<210> SEQ ID NO 39
<211> LENGTH: 20
<212> TYPE: DNA
<213> ORGANISM: Artificial Sequence
<220> FEATURE:
<223> OTHER INFORMATION: primer

<400> SEQUENCE: 39
tcgcgctctg aatcgttctg                                                   20

<210> SEQ ID NO 40
<211> LENGTH: 30
<212> TYPE: DNA
<213> ORGANISM: Artificial Sequence
<220> FEATURE:
<223> OTHER INFORMATION: primer

<400> SEQUENCE: 40
gagaacaatt gtatggcatc gccgctggtt                                        30

<210> SEQ ID NO 41
<211> LENGTH: 35
<212> TYPE: DNA
<213> ORGANISM: Artificial Sequence
<220> FEATURE:
<223> OTHER INFORMATION: primer

<400> SEQUENCE: 41
tcttctaagc ttcactaatt catgtcgtct gggtt                                  35

<210> SEQ ID NO 42
<211> LENGTH: 21
<212> TYPE: DNA
<213> ORGANISM: Artificial Sequence
<220> FEATURE:
<223> OTHER INFORMATION: oligonucleotide

<400> SEQUENCE: 42
atcagggttc gaagactgtg g                                                 21

<210> SEQ ID NO 43
<211> LENGTH: 22
<212> TYPE: DNA
<213> ORGANISM: Artificial Sequence
<220> FEATURE:

```
<223> OTHER INFORMATION: oligonucleotide

<400> SEQUENCE: 43
tcttcgaacc ctgatcaact tg                                              22
```